US011442538B2

(12) United States Patent
Douglas

(10) Patent No.: US 11,442,538 B2
(45) Date of Patent: Sep. 13, 2022

(54) VISUALIZATION OF IMAGES VIA AN ENHANCED EYE TRACKING SYSTEM

(71) Applicant: Robert Edwin Douglas, Winter Park, FL (US)

(72) Inventor: Robert Edwin Douglas, Winter Park, FL (US)

(73) Assignee: RED PACS, LLC, Winter Park, FL (US)

( * ) Notice: Subject to any disclaimer, the term of this patent is extended or adjusted under 35 U.S.C. 154(b) by 170 days.

(21) Appl. No.: 16/936,293

(22) Filed: Jul. 22, 2020

(65) Prior Publication Data

US 2021/0157399 A1 May 27, 2021

Related U.S. Application Data

(63) Continuation-in-part of application No. 16/879,758, filed on May 21, 2020, now Pat. No. 10,776,989, and a continuation-in-part of application No. 16/842,631, filed on Apr. 7, 2020, now Pat. No. 11,003,342.

(60) Provisional application No. 62/985,363, filed on Mar. 5, 2020, provisional application No. 62/939,685, filed on Nov. 25, 2019.

(51) Int. Cl.
*G06F 3/01* (2006.01)

(52) U.S. Cl.
CPC .................................. *G06F 3/013* (2013.01)

(58) Field of Classification Search
CPC ......... G06T 7/0012; G06T 2207/30041; G06T 2207/30004; G06T 2207/10132; G06T 2207/10116; G06T 2207/10072; G06T 2207/10068; G06V 2201/03; G16H 15/00; G16H 30/40
See application file for complete search history.

(56) References Cited

U.S. PATENT DOCUMENTS

| | | | | |
|---|---|---|---|---|
| 8,020,993 B1 * | 9/2011 | Fram | ...................... | G06F 3/013 351/200 |
| 2014/0307067 A1 * | 10/2014 | Douglas | ............... | H04N 13/344 348/53 |
| 2021/0264212 A1 * | 8/2021 | Paik | ..................... | G06K 9/6201 |

* cited by examiner

*Primary Examiner* — Ross Varndell

(57) ABSTRACT

In this patent, an improved eye tracking system is implemented for enhanced viewing. This system incorporates eye facing cameras and tracks display settings longitudinally and determines which portions of the image have been viewing and to what extent. A longitudinal dataset is generated and analyzed to better understand the human review process and cause improvements thereof. Furthermore, image review is enhanced by highlighting portions of the image that have not been adequately reviewed. Comparison across multiple reviewers is also performed to improve a user's performance.

17 Claims, 26 Drawing Sheets

OVERVIEW

Prepare dataset (e.g., perform segmentation of the imaging dataset so that the image is segmented into various imaging findings, perform desired visual representation adjustment logic) and display image(s)
100

Perform head and eye tracking and determine the pixel (or pixels) on the monitor (e.g., which specific monitor coordinates) where the user is looking and additional metrics (length of time, number of fixation points, etc.)
101

Determine which imaging findings user is looking at (e.g., use monitor-image conversion key to account for zoom status and pan status and correlating the fixation location on the monitor to the imaging feature)
102

Record data in longitudinal dataset along with other imaging features (e.g., mouse location, set of display settings, determine which anatomic structures are being examined, determine the length of time which anatomic structures are being examined, viewing parameters)
103

Analyzing the data & providing feedback to the user (e.g., display a modified image)
104

Figure 1

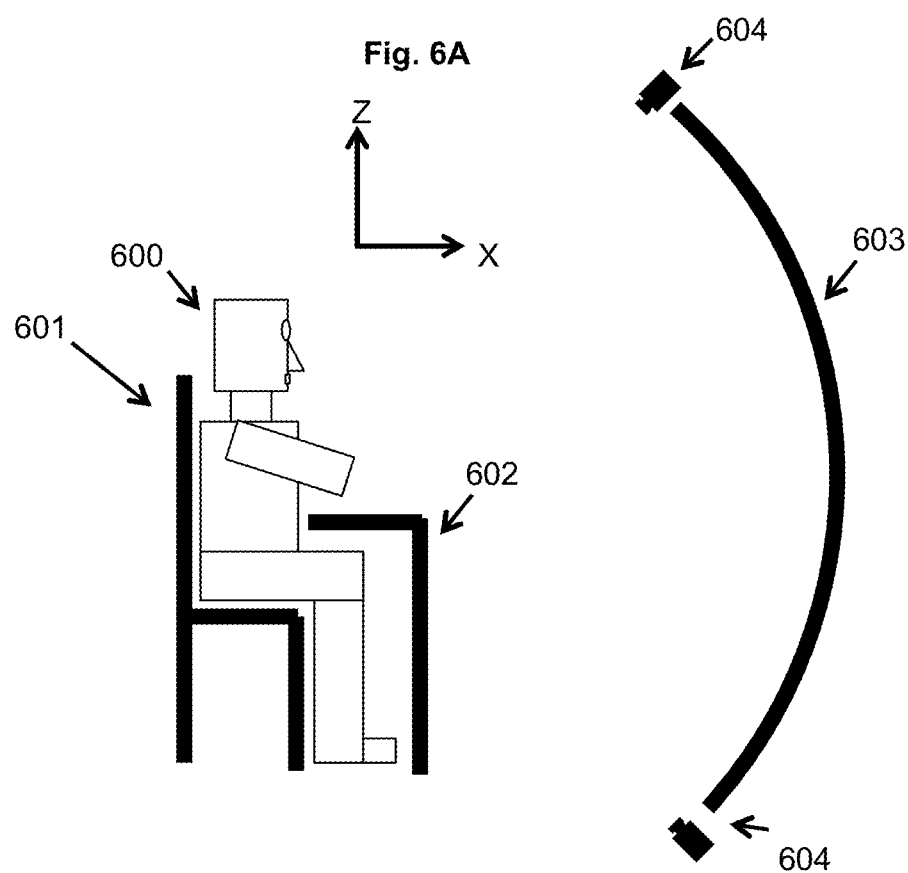
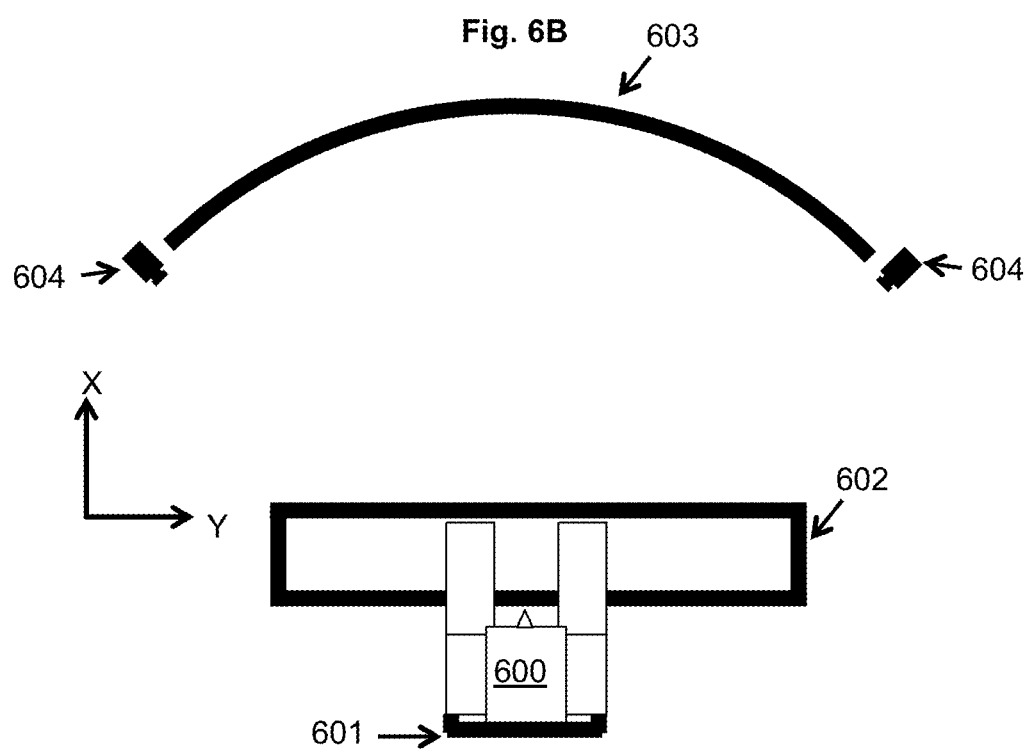

1200

| Time point (in seconds) | Conversion Key (X monitor coordinate) | Conversion Key (X image coordinate) | X conversion key (accounts for pan) | X-coordinate of eye tracking on monitor | X-coordinate of eye tracking on image |
|---|---|---|---|---|---|
| 0 | 100 | 1 | -99 | 200 | 101 |
| 0.01 | 100 | 1 | -99 | 200 | 101 |
| 0.02 | 100 | 1 | -99 | 202 | 103 |
| 0.03 | 100 | 1 | -99 | 213 | 114 |
| 0.04 | 100 | 1 | -99 | 215 | 116 |
| 0.05 | 100 | 1 | -99 | 217 | 118 |

1201

| Time point (in seconds) | Conversion Key (Y monitor coordinate) | Conversion Key (Y image coordinate) | Y conversion key (accounts for pan) | Y-coordinate of eye tracking on monitor | Y-coordinate of eye tracking on image |
|---|---|---|---|---|---|
| 0 | 100 | 1 | -99 | 200 | 101 |
| 0.01 | 101 | 1 | -100 | 201 | 101 |
| 0.02 | 102 | 1 | -101 | 205 | 104 |
| 0.03 | 103 | 1 | -102 | 240 | 138 |
| 0.04 | 103 | 1 | -102 | 242 | 140 |
| 0.05 | 103 | 1 | -102 | 241 | 139 |

Figure 12

| Time point | Conversion key | | | Input by user | Mouse location | Eye tracking coordinate on monitor | Calculated | |
|---|---|---|---|---|---|---|---|---|
| | Computer Monitor Coordinate | Image Coordinate | Zoom factor | | | | Eye tracking coordinate on image | Anatomic structure viewed |
| 0.00 sec | (100, 100) | (1, 1) | 1x | N/A | (150, 150) | (200, 200) | (101, 101) | radius |
| 0.01 sec | (100, 101) | (1, 1) | 1x | pan | (150, 151) | (200, 201) | (101, 101) | radius |
| 0.02 sec | (100, 102) | (1, 1) | 1x | pan | (150, 152) | (202, 205) | (103, 104) | radius |
| 0.03 sec | (100, 103) | (1, 1) | 1x | pan | (150, 153) | (213, 240) | (114, 138) | ulna |
| 0.04 sec | (100, 103) | (1, 1) | 1x | W/L | (150, 153) | (215, 242) | (116, 140) | ulna |
| 0.05 sec | (100, 103) | (1, 1) | 1x | W/L | (150, 153) | (217, 241) | (118, 139) | ulna |

Figure 13

ALTERING DISPLAY SETTINGS

Generating a list of optimal viewing settings for each item in an image
1400

Determining the structure that is located at each viewing location (e.g., pixel on 2D monitor or 3D point in space corresponds to liver)
1401

Initiating an eye-tracker system with an eye-facing camera(s)
1402

Recording eye-movement data with the said eye-facing camera(s)
1403

Performing analysis of the eye-movement data to determine where the user is looking (e.g., the focal point)
1404

Performing analysis of where the user is looking to determine which object the user is examining (e.g., using monitor-image conversion key)
1405

Comparing current image viewing settings with optimal viewing settings for the item in an image being examined to determine whether the viewed object is optimally displayed to the user
1406 if the viewed object is already optimally displayed to the user, no changes to the image would be performed
1407 if the viewed object is not already optimally displayed to the user, manipulate image such that it is optimally displayed (e.g., smart zoom, smart pan, smart window / level, etc.)
1408

Continuing eye tracking and optimization of display settings
1409

Figure 14

EYE TRACKING PERFORMED AND IMAGE ADJUSTMENT MADE

Perform analysis of the eye-movement data to determine where the user is looking (e.g., pixel located at row 600, column 600of the 2048 x 1536 display).
1600

Perform analysis of where the user is looking to determine which object the user is looking at (e.g., spleen).
1601

Compare current image viewing settings (e.g., optimized for viewing of the liver) with optimal viewing settings for structure in previous step (e.g., since the user is looking at the spleen, the image settings should be optimized for the spleen) and conclude that viewed object is not currently optimally displayed to the user.
1602

Change the image settings from the previous settings (e.g., from being optimized for viewing of the liver) to the new image settings (e.g., being optimized for the spleen).
1603

Figure 16

OPTIMAL VIEWING SETTINGS FOR EACH ITEM IN AN IMAGE

1800

| Item viewed | Optimal settings during 2D imaging |
|---|---|
| Liver | e.g., Liver is shaded as a rainbow color scheme. All other tissues are turned to dark gray shades. |
| Bone | e.g., Bone is colored ranging from medium gray to very light gray. All other tissues are turned to dark gray shades. |

1801

| Item viewed | Optimal settings during 3D imaging (e.g., using Augmented Reality headset) |
|---|---|
| Liver | e.g., Bands-wise prioritization of HU ranges is utilized within the liver and displayed in a dynamic fashion to make more subtle (but dangerous lesions) easier to detect. All other tissues are made more translucent (e.g., sparse sampling) or are filtered. |
| Bone | e.g., Prioritized volume rendering is performed wherein the bone surface is displayed unless the is a lesion within the central aspect of the bone, which would then be higher priority and be displayed. All other tissues are made more translucent (e.g., sparse sampling) or are filtered. |

Figure 18

CHANGING OF THE APPEARANCE OF AN IMAGE BASED ON EYE TRACKING

CHANGING OF THE APPEARANCE OF AN IMAGE BASED ON EYE TRACKING

Display image with a first example set of parameters (e.g., soft tissue window)

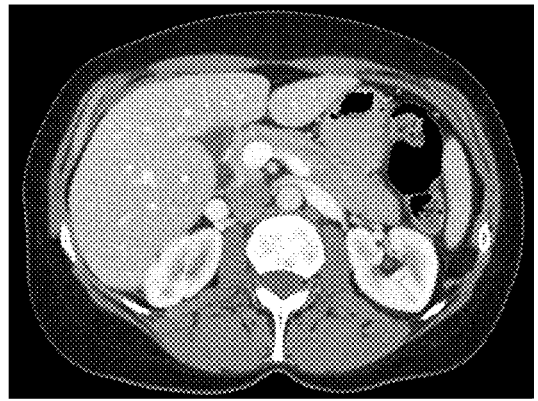

2000

Move to a segmented item to be analyzed (e.g., via eye tracking is performed and it is determined that the user is closely inspecting the pancreas, etc.)
2001

Adjust display settings of the segmented item to be analyzed to optimize viewing of the item and option to also adjust display settings of segmented items not currently being analyzed

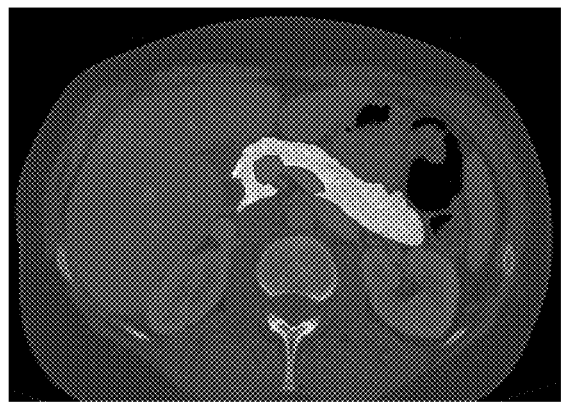

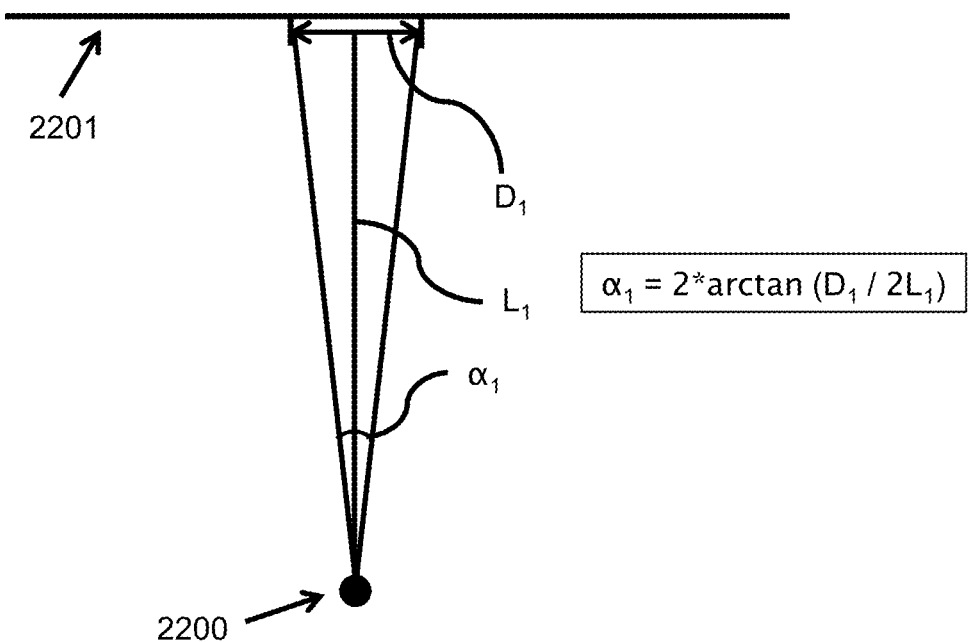
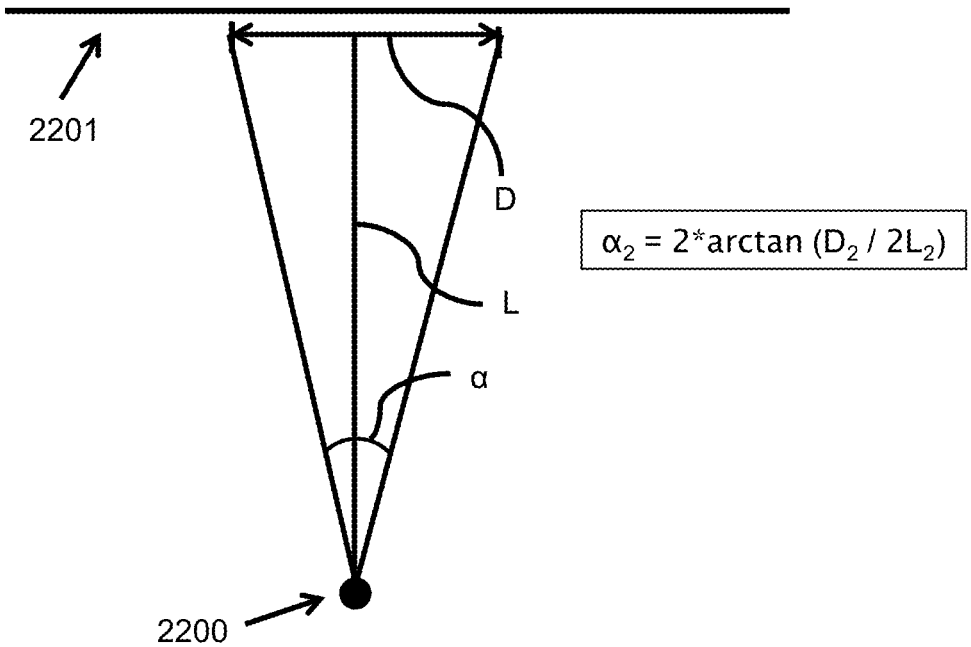
Note: figures are not drawn to scale

Fig. 23A

| Time point | What is covered in high resolution FOV | What is covered in medium resolution FOV | What is covered in low resolution FOV |
|---|---|---|---|
| 0.01 sec | Set A | Set B | Set C |
| 0.02 sec | Set D | Set E | Set F |
| 0.03 sec | Set G | Set H | Set I |
| 0.04 sec | Set J | Set K | Set L |

Fig. 23B

| | | | | | | | |
|---|---|---|---|---|---|---|---|
| B | B | B | B | B | B | B | B |
| B | B | B | A | A | B | B | B |
| B | B | A | A | A | A | B | B |
| B | A | A | A | A | A | A | B |
| B | A | A | A | A | A | A | B |
| B | B | A | A | A | A | B | B |
| B | B | B | A | A | B | B | B |
| B | B | B | B | B | B | B | B |

DETERMINING EXTENT OF REVIEW

Determining metrics (e.g., imaging features thoroughly viewed, imaging features not examined).
2400

Displaying an imaging dataset on a monitor to a user
2401

Performing segmentation of the imaging dataset (e.g., segment a brain MRI into the frontal lobe, temporal lobe, pituitary gland, etc.)
2402

Determining the location(s) of imaging features on the monitor (e.g., performed in a dynamic fashion wherein an imaging finding may change in position over time during zooming or panning by a user)
2403

Tracking eye movements of a user to determine the fixation locations at pixels on the monitor and the corresponding imaging features being viewed
2404

Recording data on fixation locations and discrete imaging features (e.g., sequence of viewing of imaging features, length of time an imaging feature has been viewed, etc.)
2405

Analyzing the recorded data on fixation locations and discrete imaging features.
2406

Reporting metrics to user.
2407

Alter imaging display based on metrics above (e.g., make imaging features not sufficiently viewed based on predetermined standards stand out in such a way as to draw the user's attention)
2408

Figure 24

THE MINIMUM REVIEW

Performing eye-tracking with an eye-facing camera to determine a set of fixation locations in the monitor
2500

Correlating the fixation locations to their corresponding imaging features
2501

Determining which predetermined locations have been viewed and which predetermined locations have not been viewed
2502

Alerting user of those predetermined locations which have not been viewed. For example:
- providing a visual alert cue adjacent to those predetermined locations which have not been viewed
- providing a first visual representation adjustment logic for the pixels nearby the predetermined locations which have been viewed and a second visual representation adjustment logic for those pixels nearby the predetermined locations which have not been viewed
2503

Figure 25

THE MINIMUM REVIEW

Example criteria a minimum number of fixation locations for the imaging dataset:
- a minimum number of fixation locations for each imaging feature (e.g., 5 fixation locations within 10 mm of the central point of the pituitary gland)
- a minimum number of fixation locations for each subsegmented spot within an imaging feature
- a minimum length of fixation location for each imaging feature
- a minimum number of imaging planes an imaging feature has fixation locations in situations comprising wherein the imaging dataset comprises cross-sectional imaging planes
- whether or not the imaging structure had optimized display during a fixation location
- whether or not a predetermined sequence of fixation locations for each imaging feature has been achieved

2600

Altering the displayed image based on the relationship between the analyzed data and the predetermined threshold
2601

Altering the brightness of imaging feature(s) that have met the predetermined threshold wherein the imaging feature(s) that have met the predetermined threshold are assigned a first visual representation adjustment logic
2602

Altering the brightness of imaging feature(s) that have not met the predetermined threshold wherein the imaging feature(s) that have not met the predetermined threshold are assigned a second visual representation adjustment logic.
2603

Figure 26 ical field.

VISUALIZATION OF IMAGES VIA AN ENHANCED EYE TRACKING SYSTEM

CROSS REFERENCES TO RELATED APPLICATIONS

This patent application is a continuation-in-part of U.S. patent application Ser. No. 16/879,758 filed on May 21, 2020 and U.S. patent application Ser. No. 16/842,631 filed on Apr. 7, 2020. In addition, this patent application claims the benefit of U.S. Provisional Patent Application 62/856,185 filed on Jun. 3, 2019, U.S. Provisional Patent Application 62/985,363 filed on Mar. 5, 1920 and U.S. Provisional Patent Application 62/939,685 filed on Nov. 25, 2019.

TECHNICAL FIELD

Aspects of this disclosure are generally related to image processing.

INTRODUCTION

Many occupations rely on work with a computer and utilize image processing. For example, an air traffic controller, a radiologist, a software engineer and others.

SUMMARY

All examples, aspects and features mentioned in this document can be combined in any technically conceivable way.

The primary purpose of this patent is to improve a radiologist's ability to analyze images through incorporation of eye tracking. More specifically, a radiologist's eyes will be tracked with an eye tracking camera. A variety of eye tracking systems can be used. For example, the head mounted Eyelink II or remoteEyeLink 1000 eye tracking system (SR Research Ltd., Ottawa, Ontario, Canada), sampled monocularly at 500 Hz. Error is within 1 degree. Example system parameters include: acceleration threshold of 9000 degrees per $sec^2$; velocity threshold of 30 degrees per sec; and deflection threshold of 0.1 degree. The metrics from the eye tracking camera will be utilized to optimize the image. The details of this process are disclosed herein.

In summary, this patent teaches a method comprises displaying an imaging dataset on a monitor to a user. Then, perform segmentation of the imaging dataset into discrete imaging features. This can be done by conventional segmentation tools (e.g., for the brain, the FreeSurfer tool can be implemented for segmentation for brain datasets). Then, determine the location(s) of imaging features on the monitor. Then, track eye movements of a user to determine the fixation locations at pixels on the monitor and the corresponding imaging features being viewed. It is important to note that a key step in this process is adjusting for image panning and zooming. This is because the image is not on a fixed location on the screen. Therefore, tracking of a user's eyes to determine a fixation location on a monitor, tracking of the image location on the monitor and tracking the image size on the monitor are performed. Then, record data on fixation locations and discrete imaging features. Then, analyzing the recorded data on fixation locations and discrete imaging features.

In order to optimize the image being viewed based on eye tracking metrics, a longitudinal dataset is generated. Metrics correlating fixation locations with imaging features are created. First, one metric is whether or not an imaging feature has at least one fixation location. For example, it would be important to have at least one fixation location on the optic nerve insertion on the eyeball because this is a critical area of importance to a radiologist. Additionally, the pituitary stalk is a small structure less than 3 mm wide (in the transverse direction). This structure, while small, is important because it can harbor a variety of pathologies. Thus, this technique of determining whether the pituitary stalk has at least one fixation location is useful. Next, it would be important to have the number of fixation locations for an imaging feature a metric. For example, a minimum number of fixation points should be on the kidney is correlated to the minimum adequate review. Additionally, if a particular imaging feature has an excess number, then it could be an indicator for pathology. For example, if the right optic nerve has been viewed with 50 fixation locations, but the average number of fixation locations for a population of imagers is 3 with a standard deviation of 2, then it would be determined that the particular imaging feature has been viewed an excess number of times and this could be an indicator of pathology. This indicator can be used further by AI/machine learning processes as well. For example, the length of time of each fixation location is also correlated to the minimum adequate review. In addition, the length of time of each fixation location is also a useful metric. For example, typical fixation duration are on the order of ~200 msec. If a single fixation duration is found to be on the order of ~800 msec or longer, then it could be flagged as a spot that is at a higher risk of harboring pathology. Next, the location within an imaging feature of each fixation location is a metric. It is not enough to document a single fixation point in the pituitary gland, a fixation location on the small posterior pituitary bright spot is also important. For example, common spots within the lateral ventricle on a CT scan of the head include the posterior aspects of the occipital horns. If an atypical location was viewed (e.g., the central portion of the frontal horn of the lateral ventricle well away from the ependymal lining), then this imaging feature can be flagged as higher risk and more likely to harbor pathology. Next, an adequate review demands that a radiologist review an imaging feature on multiple imaging planes (e.g., common bile duct); therefore, the number of imaging planes an imaging feature has fixation locations in situations comprising wherein the imaging dataset comprises cross-sectional imaging planes is an important metric. For example, if that same spot in the frontal horn of the lateral ventricle were viewed on all three planes in an excessive fashion, then that spot may be determined to be high risk. For example, the sequence of fixation locations and viewing of imaging features is also important, as this indicate a search pattern of cause and effect. For example, if a radiologist were to notice a skull fracture, the radiologist should do a deliberate search for an epidural hematoma. These such metrics are utilized in accordance with U.S. patent application Ser. No. 16/842,631, A SMART SCROLLING SYSTEM, which is incorporated by reference. Additionally, a typical sequence could be oscillating medial-lateral and moving in an inferior fashion down the right lung and then oscillating medial-lateral and moving in a superior fashion up the left lung. If this sequence was maintained, that could be an indicator that the study is normal. If this sequence was broken, it could indicate that there is an abnormality within the image. Alternatively, it could indicated that there was an interruption (e.g., phone call). Finally, time of review per segmented structure and total time are additional metrics recorded.

In some embodiments, comparing the longitudinal dataset with a predetermined criteria to determine extent of review.

Examples of predetermined criteria include, but are not limited to, the following: a minimum number of fixation locations for the imaging dataset; a minimum number of fixation locations for each imaging feature; a minimum number of fixation locations for each subsegmented area (e.g., head of the pancreas) within an imaging feature (e.g., pancreas); a minimum time of fixation location for each imaging feature; a minimum number of imaging planes an imaging feature has fixation locations in situations comprising wherein the imaging dataset comprises cross-sectional imaging planes; whether or not the imaging structure had optimized display during a fixation location; and whether or not a predetermined sequence of fixation locations for each imaging feature has been achieved.

In some embodiments, data is averaged from each metric over a set of imaging datasets to determine an average for each metric for the user. For example, the same metrics can be obtained on the same user for review of 100 non-contrast head CT exams. In some embodiments, a notification to the user is performed when a metric for the imaging examination differs from the average for each metric for the user. For example, assume that the average time period for the user to look at the midline sagittal image of the brain was 10.5 seconds and assume that there was no case in the past 100 cases where the user had viewed the midline sagittal image for less than 8 seconds. Assume that the user viewed the midline sagittal image for 0.1 seconds. That would be a significant deviation of the normal. It could be related to a variety of user errors (e.g., phone call). The method would alert the user of this anomaly and allow for the opportunity to correct the error.

Some embodiments further comprising averaging data from each metric over a set of imaging datasets to determine an average for each metric for a population of users to develop a set of normative metrics. Comparison of a user's metrics to a population dataset can be performed to bring out deviations from the normal. As a result, the user can learn and improve.

The preferred embodiment is a method of altering display settings based on information from eye-tracking technology. A list of optimal viewing settings for each item in an image is generated. The item that is located at each viewing location (e.g., pixel on 2D monitor or 3D point in space corresponds to liver) is determined. An eye-tracker system with at least one eye-facing camera is initiated. Eye-movement data with the said eye-facing camera(s) is recorded. Analysis of the eye-movement data to determine where the user is looking (e.g., the focal point) is performed. Analysis of where the user is looking to determine which object the user is examining is performed. The current image viewing settings with optimal viewing settings for the item in an image being examined is performed to determine whether the viewed object is optimally displayed to the user. If the viewed object is already optimally displayed to the user, no changes to the image would be performed. If the viewed object is not already optimally displayed to the user, manipulate image such that it is optimally displayed. Finally, eye tracking and optimization of display settings is continued. The eye tracking techniques can cause 2D datasets (e.g., chest radiograph) or 3D datasets (e.g., Computed Tomography scan slices) to be optimized. The eye tracking techniques can be performed in conjunction with 2D displays (e.g., conventional 2D radiology monitors), advanced curved monitors (single curve or double curved) or extended reality head displays.

Some embodiments comprise altering the displayed image based on the relationship between the analyzed data and the predetermined criteria. An example includes altering the brightness of imaging feature(s) based on whether or not the predetermined criteria for the imaging feature has been met. For example, an imaging feature(s) that has been met the predetermined threshold is assigned a first visual representation adjustment logic (dark shades of gray) and an imaging feature(s) that have not met the predetermined threshold is assigned a second visual representation adjustment logic (bright shades of gray).

Some embodiments comprise providing visual feedback to the user on predetermined criteria to assure that the user performs a comprehensive review of the imaging dataset. Examples include, but are not limited to, the following: circles; annotations; and, arrows.

Some embodiments comprise performing eye tracking, which causes some areas within the image to be viewed to be displayed with variable display settings. Examples of the user preferred display settings include: windowing and leveling of at least one portion of an image; kernel (e.g., bone kernel to soft tissue kernel) of at least one portion of an image; color of at least one portion of an image; voxel prioritization, as described in U.S. patent application Ser. No. 16/879,758, A METHOD AND APPARATUS FOR PRIORITIZED VOLUME RENDERING of at least one portion of an image; band-wide grouping of at least one portion of an image, as described in U.S. Pat. No. 10,586,400, PROCESSING 3D MEDICAL IMAGES TO ENHANCE VISUALIZATION, which is incorporated by reference; filtering of at least one portion of an image; latency (how long the user should look at an object prior to the image display settings being manipulated); technique on switching to new image display settings (fading in the new image settings slowly or immediately in a subsequent frame show the new image).

Some embodiments comprise utilization of inputs from a user's hands (e.g., via controller, keyboard, hand gestures, etc.) to guide/override whether or not to change settings to a more optimal viewing can be based on eye position. Examples of the settings are previously described.

In some embodiments, the cameras assess the user's face for facial expressions, which may be indicative of a lesion. If such a facial expression is identified, then this can be brought to the attention of the user (e.g., radiologist) during report generation.

Given that the majority of radiology departments still use flat screen monitors, this patent's process is anticipated to be first used on existing monitors. Eye-facing cameras can be incorporated. It is envisioned that future embodiments comprise wherein the monitor has a curvature comprising: the top portion of the monitor curves inwards towards the user; the bottom portion of the monitor curves inwards towards the user; the left portion of the monitor curves inward towards the user; and the right portion of the monitor curves inward towards the user. A wide range of images can be displayed on this "double curved" monitor to enhance viewing. Examples include conventional viewing of radiological images and advanced viewing techniques as disclosed in this patent. Some embodiments further comprise utilizing a head display unit (HDU) comprising at least one of an extended reality display, shutter lenses and polarized lenses wherein the HDU provides a 3D image to the user. Furthermore, more ergonomic keyboards are also utilized with the middle of the keyboard elevated as compared to the sides so as to reduce the required pronation during typing.

Some embodiments comprise a monitor-image conversion key. In this embodiment, a monitor coordinate system is established. Then, at each time point in the dataset, at least one data point within an image wherein the at least one data point within an image serves as a reference point for all other data points within the image. Furthermore, at each point in the dataset, a recording the zoom state of the image is performed. Additionally, eye tracking is performed to determine a user's fixation location on the monitor coordinate system. Using the monitor-image conversion key, which data point within the image corresponds to which fixation location can be determined.

Some embodiments comprise assigning a set of predetermined locations within an image that should be viewed by a user in order for a comprehensive review to be performed. For example, the pituitary stalk could be a predetermined location that should be viewed. In the event that the user has the minimum number of fixation points on the pituitary stalk, this criteria would be satisfied. However, if the predetermined location (e.g., pituitary stalk) was not visualized, options include creating a reminder (e.g., stating "look at pituitary stalk"), presenting the predetermined location (e.g., sagittal midline image showing the pituitary stalk), or combination thereof.

Some embodiments comprising wherein the user is alerted of those predetermined locations which have not been viewed by at least one of the group comprising: providing a visual alert cue adjacent to those predetermined locations which have not been viewed; and providing a first visual representation adjustment logic for the pixels nearby the predetermined locations which have been viewed and a second visual representation adjustment logic for those pixels nearby the predetermined locations which have not been viewed. Thus, this system may incorporate imaging findings on a radiologist's checklist.

Some embodiments incorporate digital objects in proximity to a predetermined location that has not been viewed, so as to draw the user's attention to the predetermined location and provide a more comprehensive view.

Some embodiments comprise using artificial intelligence algorithms to understand the correlation between eye movements and pathological conditions.

Some embodiments comprise performing "smart panning" based on eye tracking. In this embodiment, eye tracking data can cause the displayed image to pan to a new location. For example, if the user is looking at a particular region, the "smart panning" function can be implemented to pan the image to a new location. For example, if the user is looking at a finding with numerous fixation locations (e.g., meets a predetermined criteria of number of fixation spots) on an imaging finding (e.g., humerus bone on a chest x-ray) within a predetermined location (e.g., distance to the edge of the monitor is less than 1 inch), then the smart panning function can be implemented. This can be done automatically and the entire image can be moved inward from the edge of the monitor so that the user can see it better.

Some embodiments comprise performing "smart zooming" based on eye tracking. In this embodiment, eye tracking data can cause the displayed image to zoom to a new size (smaller or bigger). For example, if the user is looking at a very tiny structure (e.g., brain aneurysm), smart zooming can enlarge the image automatically to the optimized size.

Some embodiments comprise performing "smart window/level" based on eye tracking. In this embodiment, eye tracking data can cause the image displayed in a fashion that is optimized for the structure being viewed. For example, if the user is looking at the liver, smart window/level can automatically display the liver in a liver window.

Some embodiments comprise wherein the image display setting is changed dynamically. For example, the user changes the window/level setting, scrolls through the liver, zooms, pans, changes the liver again. During this time, eye tracking data is being acquired to determine which structures the user is looking at the whole time and what display setting is shown.

Some embodiments comprise recording pupil size to determine accommodation and incorporating these data into the longitudinal dataset.

Some embodiments comprise free-viewing as no external stimuli of what imaging features should be looked at. In this embodiment, predetermined criteria can be implemented on eye movements, mouse movements, window/level settings and zoom settings, so as to assure that certain features are optimized. As previously discussed, if a predetermined criteria is not met during the free-viewing, the user can be alerted.

Some embodiments comprise a guided-viewing process, as external stimuli of what imaging features should be looked at. An example of the guided viewing process is automatic scrolling, automatic windowing/leveling, automatic panning, automatic zooming and use of digital objects to guide a user to look at certain spots in the image. A digital dot could be in the form of one or more small objects on the screen. Alternatively, the cursor could automatically move and be used as a digital object to guide the radiologist in viewing of images.

Some embodiments comprise showing a digital object at the location of a user's fixation locations. The key application of this embodiment is a teaching environment. For example, a radiology attending can watch a radiology resident's fixation locations on the screen in real time. Such an option could be performed while using augmented reality headsets. For example, user #1 could see where user #2 is looking, but user #1 would not see his own digital object (which would be a distraction). In some embodiments, a head tracking system could also be utilized in a similar fashion to perform optimization of the imagery.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing three-dimensional viewing of images by a user as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as software and hardware, or as hardware and/or circuitry alone, such as within a data communications device. The features of the invention, as explained herein, may be employed in data processing devices and/or software systems for such devices.

In some embodiments, viewing of a radiology image is performed on a monitor wherein the top portion of the monitor curves inwards towards the user, the bottom portion of the monitor curves inwards towards the user, the left portion of the monitor curves inward towards the user; and the right portion of the monitor curves inward towards the user. In some embodiments, an eye-facing camera(s) is used in conjunction with this monitor, such that eye-tracking can be performed in conjunction with these techniques. In some embodiments, a computer is used in conjunction with the eye tracking. In some embodiments, the computer performs an algorithm to record areas or volumes which have been reviewed and areas or volumes which have not been reviewed. In some embodiments, the computer displays areas or volumes which have been reviewed differently from areas or volumes which have not been reviewed. In some embodiments, techniques described in U.S. Pat. No. 10,586, 400, which is incorporated by reference.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

FIG. 1 illustrates the overview of a smart review process.
FIG. 6A illustrates a side view of the radiologist's workstation.
FIG. 6B illustrates a top-down view of the radiologist's workstation.

FIG. 12 illustrates application of the conversion key to convert where a user is looking on a computer monitor to where a user is looking on an image.
FIG. 13 illustrates generation longitudinal dataset.
FIG. 14 illustrates a method of altering display settings based on information from eye-tracking technology.
FIG. 16 illustrates an example wherein the spot at which the user is looking is not currently optimized viewing settings and changes to the viewing settings are automatically performed.
FIG. 18 illustrates generating a list of the optimal viewing settings for each item in an image.

FIG. 20 illustrates an example of changing of the appearance of an image in accordance with eye tracking.

FIG. 22A illustrates an imaging finding displayed on a monitor.

FIG. 22B illustrates an imaging finding displayed on a monitor.

FIG. 23A illustrates determining and recording which areas (e.g., voxels or pixels) are included in the high resolution field of view (FOV), which areas (e.g., voxels or pixels) are included in the medium resolution FOV, and which areas (e.g., voxels or pixels) are included in the low resolution FOV.

FIG. 23B illustrates a zoomed in 8×8 set of voxels, showing assigning some voxels to a high resolution FOV and some voxels to a medium resolution FOV in accordance with FIG. 23A.

FIG. 24 illustrates a method of generating metrics based on which imaging features have been reviewed.

FIG. 25 illustrates assigning a set of predetermined locations within an image that should be viewed by a user in order for a comprehensive review to be performed.

FIG. 26 illustrates comparing the analyzed recorded data on fixation locations and discrete imaging features with a predetermined criteria of minimum imaging metrics that must be met for a complete review.

DETAILED DESCRIPTIONS

Figure 2:
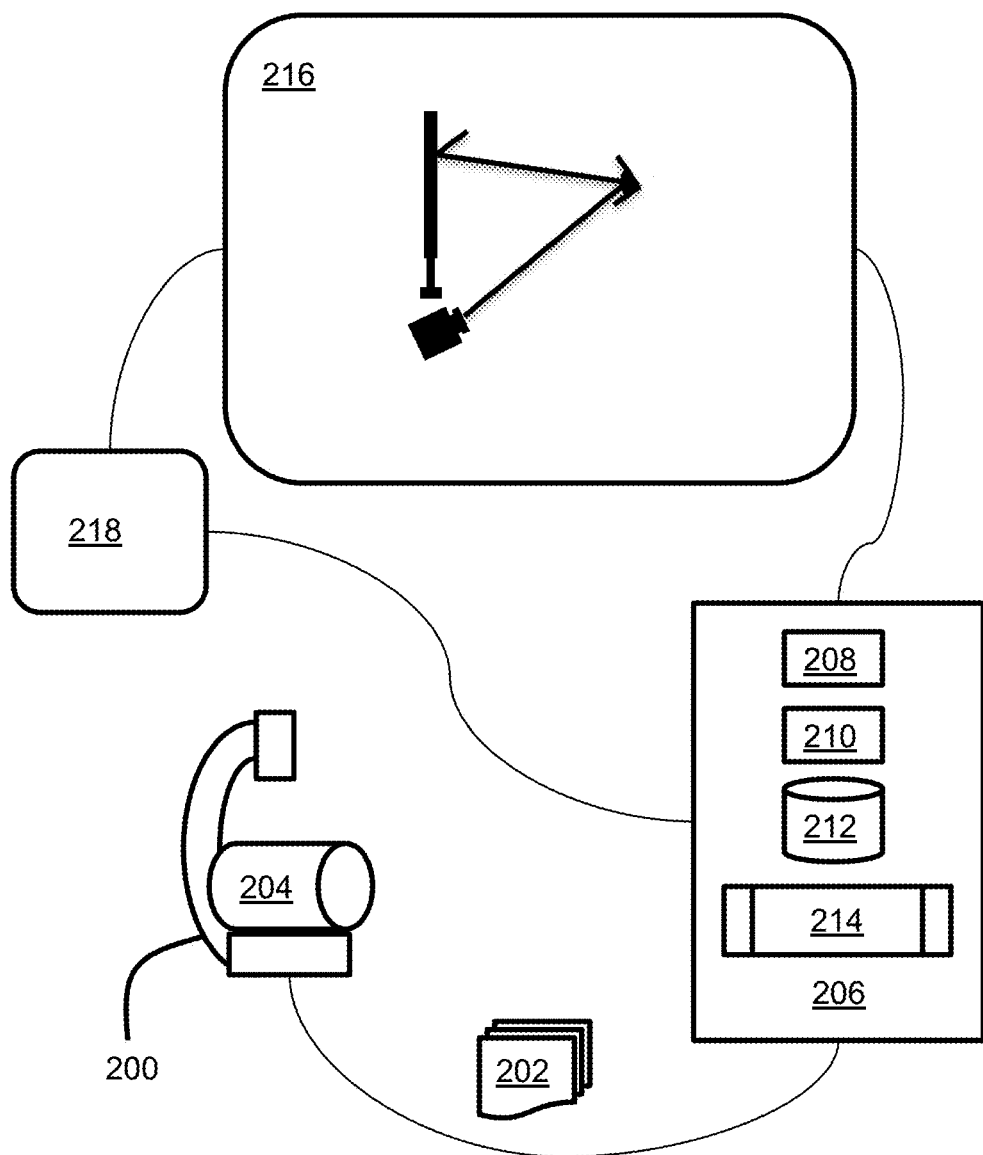
FIG. 2 illustrates an overview of the apparatus used for eye tracking in diagnostic radiology.

FIG. 1 illustrates the overview of a smart review process. Processing block 100 illustrates the step of preparing the dataset (e.g., perform segmentation of the imaging dataset so that the image is segmented into various imaging findings, perform desired visual representation adjustment logic including the set of display settings (how the image is displayed, such as window/level settings), and display image(s). Processing block 101 illustrates the step of perform head and eye tracking and determine the pixel (or pixels) on the monitor (e.g., which specific monitor coordinates) where the user is looking and additional metrics (length of time, number of fixation points, etc.). Processing block 102 illustrates the step of determining which imaging findings user is looking at (e.g., use monitor-image conversion key to account for zoom status and pan status and correlating the fixation location on the monitor to the imaging feature). Processing block 103 illustrates the step of recording data in longitudinal dataset along with other imaging features (e.g., mouse location, set of display settings, determine which anatomic structures are being examined by eye tracking, which structure is actively being studied on the radiologist's checklist, determine the length of time which anatomic structures are being examined, other viewing parameters, etc.). Processing block 104 illustrates the step of analyzing the data and providing feedback to the user (e.g., display a modified image, such as scroll to a contiguous slice for slice-by-slice review, zooming, panning, changing window and level settings, changing transparency for D3D review, etc.). Note that the modification of the image is also recorded in the longitudinal dataset.

FIG. 2 illustrates an overview of the apparatus used for eye tracking in diagnostic radiology. A radiologic imaging system 200 (e.g., X-ray, ultrasound, CT (computed Tomography), PET (Positron Emission Tomography), or MM (Magnetic Resonance Imaging)) is used to generate medical images 202 of an anatomic structure 204 of interest. The medical images 202 are provided to an image processor 206, that includes processors 208 (e.g., CPUs and GPUs), volatile memory 210 (e.g., RAM), and non-volatile storage 212 (e.g. HDDs and SSDs). A program 214 running on the image processor implements one or more of the steps described in this patent. Medical images and displayed on an IO device 216, which includes an eye tracking system. The IO device may also include a virtual or augmented reality headset, monitor, tablet computer, PDA (personal digital assistant), mobile phone, or any of a wide variety of devices, either alone or in combination. The IO device may include a touchscreen and, may accept input from external devices (represented by 218) such as a keyboard, mouse, and any of a wide variety of equipment for receiving various inputs. However, some or all the inputs could be automated, e.g. by the program 214.

Figure 3A:
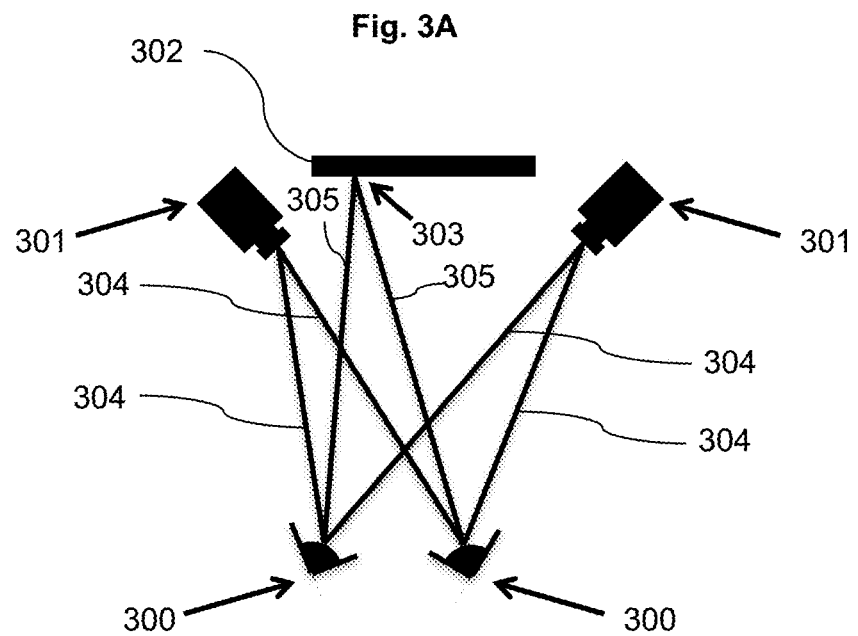
FIG. 3A illustrates a top down view is shown and the user is looking at a pixel on the left aspect of the screen.

FIG. 3A illustrates a top down view is shown and the user is looking at a pixel on the left aspect of the screen. 300 illustrates the eyes of a user. 301 illustrates cameras that perform eye tracking. 302 illustrates the monitor. 303 illustrates a pixel on the screen that a user is looking at. 304 illustrates light rays traveling from the user's eyes, which travel towards the cameras 301. 305 illustrates light rays traveling from the pixel on the screen that the user is looking at towards the user's eyes 300. The eye tracking system determines which pixel the user is looking at.

Figure 3B:
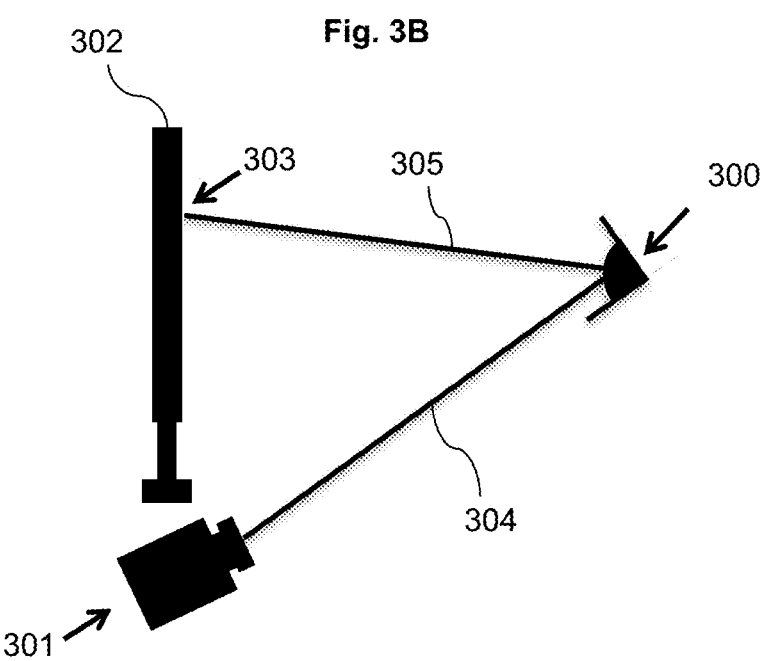
FIG. 3B illustrates a side view wherein the user is looking at a pixel near the top of the screen.

FIG. 3B illustrates a side view wherein the user is looking at a pixel near the top of the screen. 300 illustrates the eyes of a user. 301 illustrates cameras that perform eye tracking. 302 illustrates the monitor. 303 illustrates a pixel on the screen that a user is looking at. 304 illustrates light rays traveling from the user's eyes, which travel towards the cameras 301. 305 illustrates light rays traveling from the pixel on the screen that the user is looking at towards the user's eyes 300. The eye tracking system determines which pixel the user is looking at.

Figure 4A:
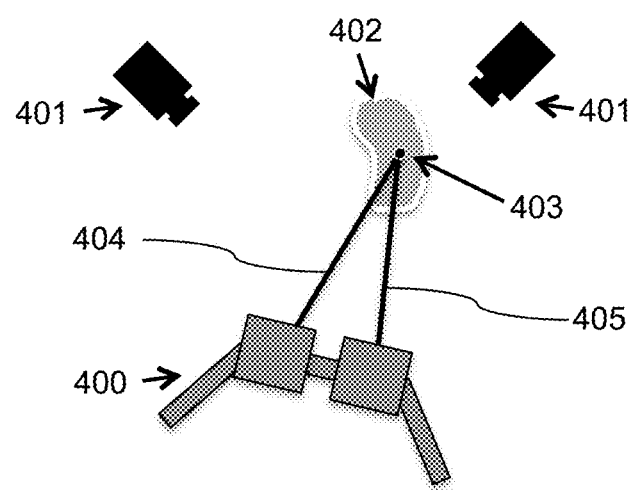
FIG. 4A illustrates an eye-tracker system with an eye-facing camera(s) working in conjunction with an extended reality headset.

FIG. 4A illustrates an eye-tracker system with an eye-facing camera(s) working in conjunction with an extended reality headset. The cameras use eye tracking and head tracking to determine that the user is gazing at a 3D point within a kidney. Therefore, the display is optimized for viewing the kidneys. This optimization includes, but is not limited to, the following: conventional gray-scale optimization (e.g., windowing and leveling); double windowing in accordance with U.S. Pat. No. 10,586,400; and prioritized volume rendering in accordance with U.S. patent application Ser. No. 16/842,631. Also, the algorithm (per user preference) states if the user is looking at one kidney, then display both kidneys with optimal display configurations. 400 illustrates an extended reality head display unit. 401 illustrates cameras which perform eye tracking. 402 illustrates the virtual image of the kidney, which the user is looking at. 403 illustrates the convergence point where the user is looking at within the kidney. 404 illustrates the line of sight from the left eye to the convergence point 403. 405 illustrates the line of sight from the right eye to the convergence point 403.

Figure 4B:
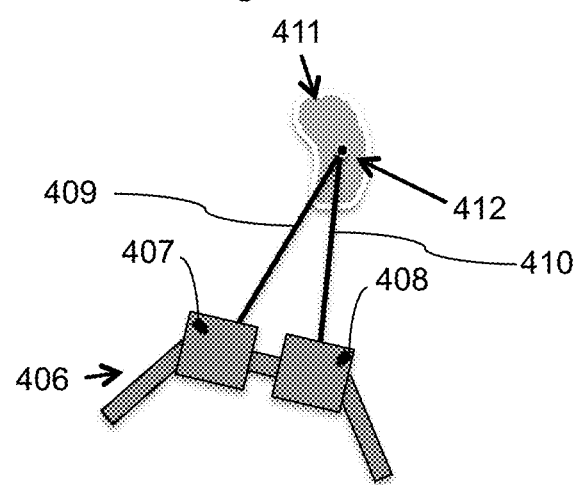
FIG. 4B illustrates an eye-tracker system an extended reality headset with an on-board with eye-facing camera(s).

FIG. 4B illustrates an eye-tracker system an extended reality headset with an on-board with eye-facing camera(s). 406 illustrates an extended reality head display unit, which contains eye tracking cameras on board the extended reality head display unit. 407 illustrates an eye tracking camera for the left eye. 408 illustrates an eye tracking camera for the right eye. 409 illustrates the line of sight from the left eye to a convergence point 412. 410 illustrates the line of sight from the right eye to the convergence point 412. 411 illustrates the virtual image of the kidney, which the user is looking at. 412 illustrates the convergence point where the user is looking at within the kidney.

Figure 5:
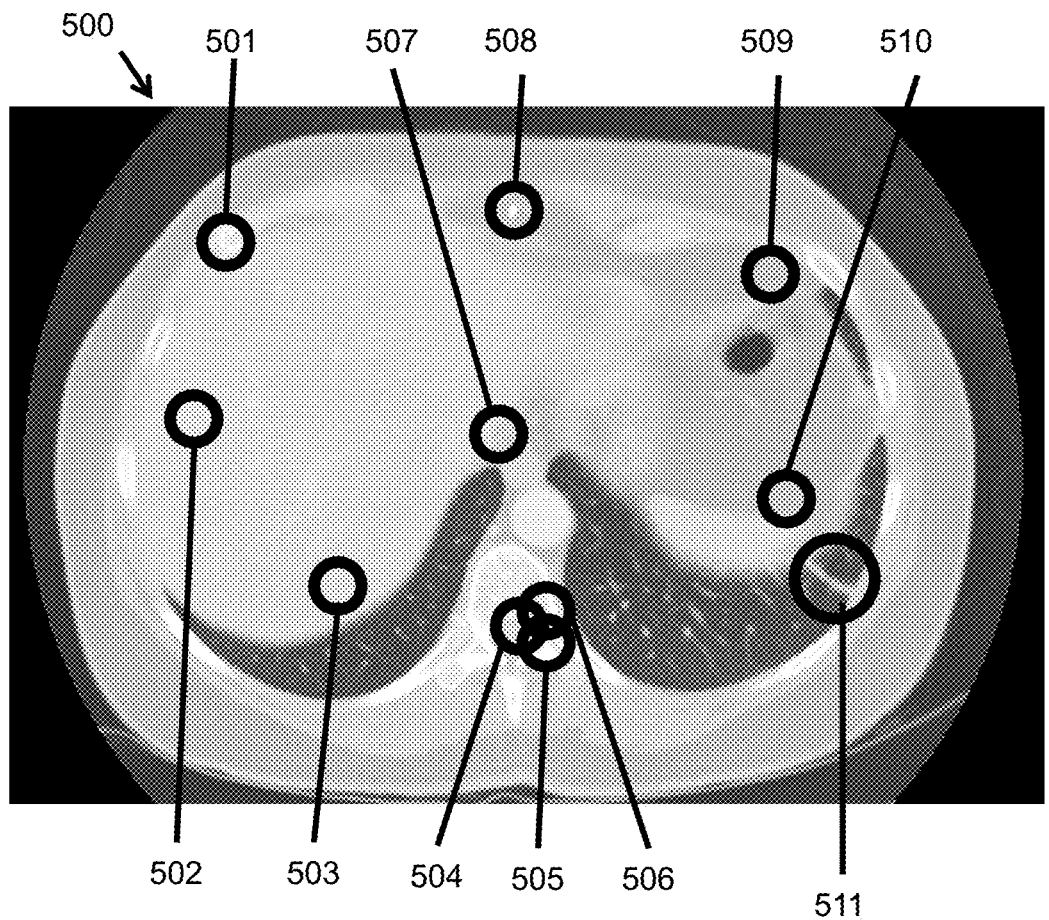
FIG. 5 illustrates fixation points illustrated on a CT scan slice through the upper abdomen identified by the eye-tracking system.

FIG. 5 illustrates fixation points illustrated on a CT scan slice through the upper abdomen identified by the eye-tracking system. 500 illustrates the CT image slice. 501 illustrates a first fixation point. 502 illustrates a second fixation point. 503 illustrates a third fixation point. 504 illustrates a fourth fixation point. 505 illustrates a fifth fixation point. 506 illustrates a sixth fixation point. 507 illustrates a seventh fixation point. 508 illustrates a eighth fixation point. 509 illustrates a ninth fixation point. 510 illustrates a tenth fixation point. 511 illustrates a eleventh fixation point. Note that it is possible for a fixation point to be on more than one slice. For example, if a user is scrolling through slices rapidly, two or more consecutive images could have a fixation point at the same point on the monitor.

FIG. 6A illustrates a side view of the radiologist's workstation. 600 illustrates a radiologist. 601 illustrates a chair that the radiologist 600 is sitting on. 602 illustrates a desk that the radiologist is using. 603 illustrates a monitor wherein the top portion of the monitor curves toward the user and the bottom of the monitor curves toward the user. 604 illustrates cameras, which perform eye tracking. A coordinate system is also shown wherein the Z-direction is vertical (i.e., upward/downward direction towards the floor) and the X-direction is horizontal in the direction from the user to the monitor 603.

FIG. 6B illustrates a top-down view of the radiologist's workstation. 600 illustrates a radiologist. 601 illustrates a chair that the radiologist 600 is sitting on. 602 illustrates a desk that the radiologist is using. 603 illustrates a monitor wherein the left portion of the monitor curves toward the user and the right portion of the monitor curves toward the user. 604 illustrates cameras, which perform eye tracking. A coordinate system is also shown wherein the Y-direction is horizontal in the left-right direction and the X-direction is horizontal in the direction from the user to the monitor 603.

Figure 7A:
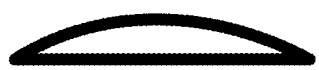
FIG. 7A is a top view of a monitor screen.

FIG. 7A is a top view of a TV/monitor screen.

Figure 7B:
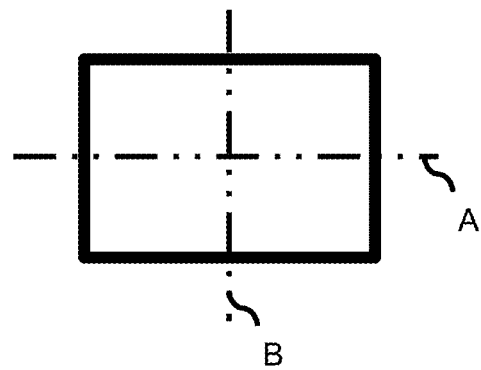
FIG. 7B is a front view of the monitor screen shown in FIG. 7A.

FIG. 7B is a front view of the TV/monitor screen shown in FIG. 7A. Note a cross-section taken along line A. Note a cross-section taken along line B.

Figure 7C:
FIG. 7C is a rear view of the monitor screen shown in FIG. 7A.

FIG. 7C is a rear view of the TV/monitor screen shown in FIG. 7A.

Figure 7D:
FIG. 7D is the right side view of the TV/monitor screen shown in FIG. 7A.

FIG. 7D is the right side view of the TV/monitor screen shown in FIG. 7A.

Figure 7E:
FIG. 7E is the left side view of the TV/monitor screen shown in FIG. 7A.

FIG. 7E is the left side view of the TV/monitor screen shown in FIG. 7A.

Figure 7F:
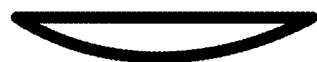
FIG. 7F is the bottom view of the TV/monitor screen shown in FIG. 7A.

FIG. 7F is the bottom view of the TV/monitor screen shown in FIG. 7A.

Figure 7G:
FIG. 7G is a cross-sectional view taken along line A in FIG. 7B.

FIG. 7G is a cross-sectional view taken along line A in FIG. 7B.

Figure 7H:
FIG. 7H is a cross-sectional view taken along line B in FIG. 7B.

FIG. 7H is a cross-sectional view taken along line B in FIG. 7B. The device is not limited to the scale shown herein. Also note that the top, bottom, left and right sides of the monitor can be comprised of straight edges or curved edges. The uniqueness of this design is the "double curved" appearance. Note that the top portion of the monitor curves inwards towards the user. Note that the bottom portion of the monitor curves inwards towards the user. Note that the left portion of the monitor curves inward towards the user. Note that the the right portion of the monitor curves inward towards the user. Different portions of the monitor would be roughly the same distance from the user's head. This solves the problem of having numerous (e.g., 8+) monitors lined up for a single user and the monitors in the center are easily seen at the best viewing distance and the monitors on the sides are poorly seen due to longer viewing distances.

Figure 8A:
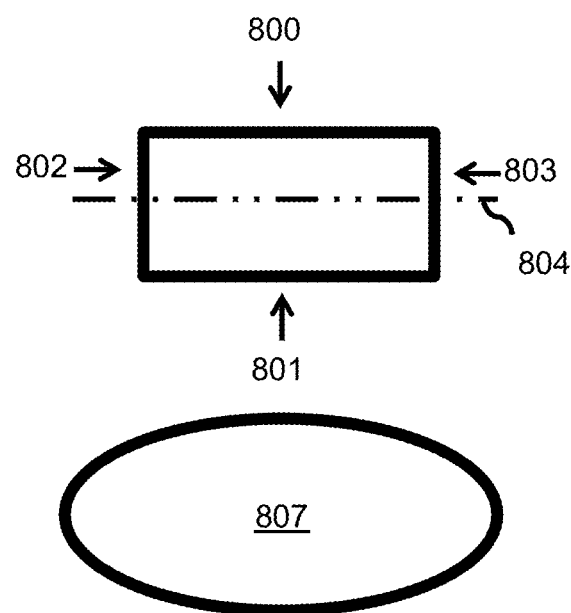
FIG. 8A is a view from the top of a keyboard (keys not shown) looking down.

FIG. 8A is a view from the top of a keyboard (keys not shown) looking down. 800 illustrates the side of the keyboard farthest away from a user's torso 807. 801 illustrates the side of the keyboard closest to a user's torso. 802 illustrates the left side of the keyboard (i.e., closest to where the left hand naturally types). 803 illustrates the right side of the keyboard (i.e., closest to where the right hand naturally types). 804 illustrates a cross-section through the keyboard.

Figure 8B:
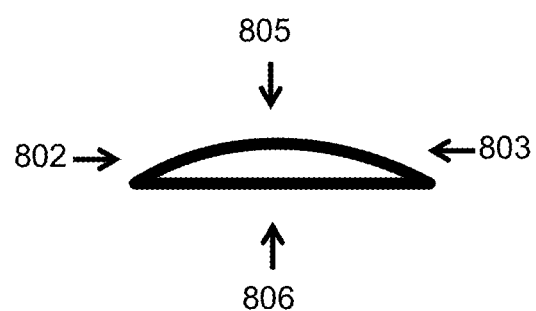
FIG. 8B is a cross-section of the keyboard.

FIG. 8B is a cross-section of the keyboard. This view is a cross-section taken along line 804 looking from the front of the keyboard (e.g., at the level of the user's torso). 802 illustrates the left side of the keyboard (i.e., closest to where the left hand types). 803 illustrates the right side of the keyboard (i.e., closest to where the right hand types). 805 illustrates the top of the keyboard (i.e., where the keys are located). 806 illustrates the bottom of the keyboard (i.e., portion that sits on and makes contact with the desk). Note that the middle of the keyboard is elevated (e.g., higher up and closer to the ceiling of a room) as compared a side (left side 802 or right side 803). This allows a user to strike the keys straight on with less total amount of forearm pronation. Some professions (e.g., radiologists) spent many hours a day at a keyboard and maximizing ergonomic keyboard would therefore have utility.

Figure 9A:
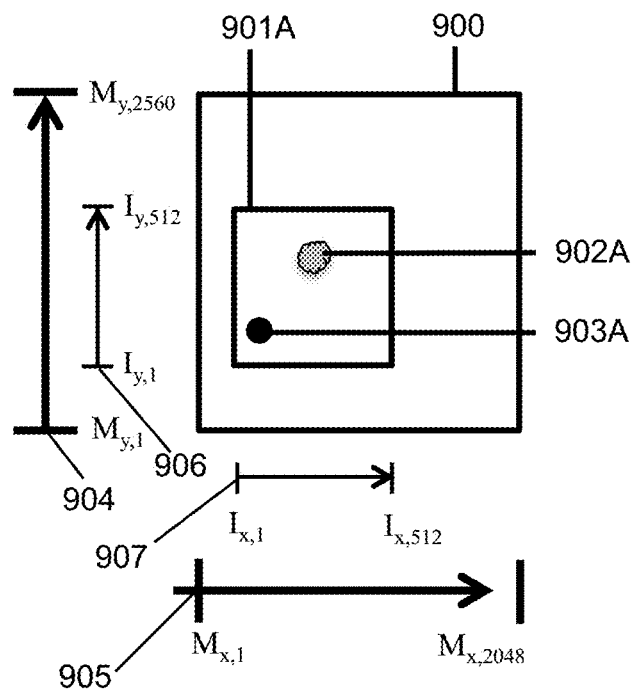
FIG. 9A illustrates an example image of a monitor illustrating the monitor coordinate system and the image coordinate system wherein the image is at a first location on the monitor.

FIG. 9A illustrates an example image of a monitor illustrating the monitor coordinate system and the image coordinate system wherein the image is at a first location on the monitor. 900 illustrates the computer monitor. 901A illustrates the image on the computer monitor at a first location. Note that it does not fill up the entirety of the computer monitor. 902A illustrates a finding of interest (a tumor) in the image 901A, which is fixed with respect to the image and a variable coordinate with respect to the monitor (note that it is variable because the user can pan and zoom, which would cause the location of the finding of interest 902A to move to different locations on the monitor and be of different sizes on the monitor). 903A illustrates the location of the computer mouse, which has a variable coordinate with respect to the image 901A (note that it is variable because the user can move it over different portions of the image) and a variable coordinate with respect to the monitor 900 (note that it is variable because the user can move it all over the monitor 900 including portions of the monitor 900 other than the image 901A). 904 illustrates the y-axis of the monitor coordinate system. In this example (modeled off of the Barco Coronis 5MP, which has an array of 2560×2048 pixels), the y-coordinates of the monitor coordinate system range from 1 to 2560. 905 illustrates the x-axis of the monitor coordinate system. In this example, the x-coordinates of the monitor coordinate system range from 1 to 2048. 906 illustrates the y-axis of the image coordinate system. In this example, the y-coordinates of the image range from 1 to 512. 907 illustrates the x-axis of the image coordinate system. In this example, the x-coordinates of the image range from 1 to 512. Thus, the tumor 902A would have a first set of image coordinates and a first set of monitor coordinates.

Figure 9B:
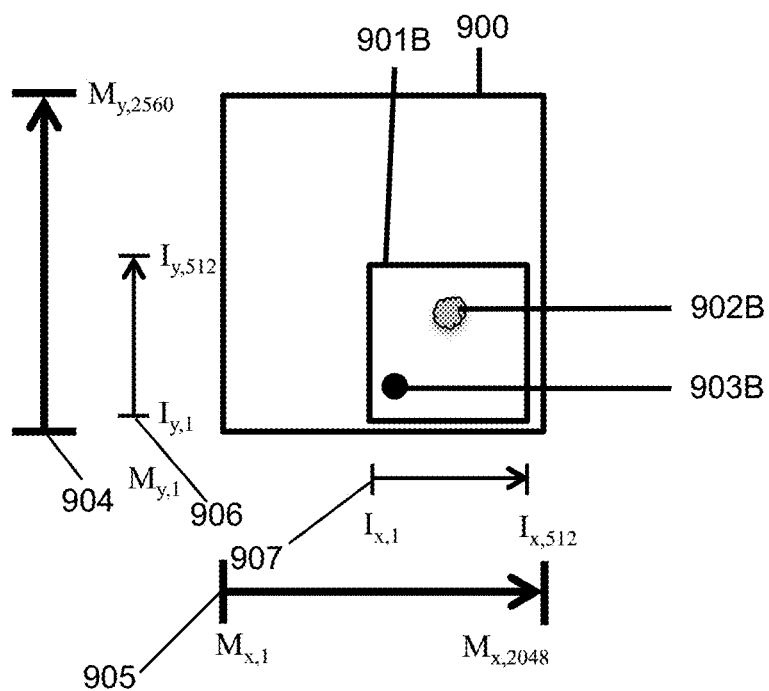
FIG. 9B illustrates an example image of a monitor illustrating the monitor coordinate system and the image coordinate system wherein the image is at a second location on the monitor.

FIG. 9B illustrates an example image of a monitor illustrating the monitor coordinate system and the image coordinate system wherein the image is at a second location on the monitor. Note that a pan function has been performed wherein the image is moved to a different location on the monitor. This can be performed during maneuvers such to better inspect certain portions of the image. 900 illustrates the computer monitor. 901B illustrates the image on the computer monitor at a second location. Note that it does not fill up the entirety of the computer monitor. 902B illustrates a finding of interest (a tumor) in the image 901B, which is fixed with respect to the image 901B and a variable coordinate with respect to the monitor 900 (note that it is variable because the user can pan and zoom, which would cause the location of the finding of interest 902B to move to different locations on the monitor 900). 903B illustrates the location of the computer mouse, which has a variable coordinate with respect to the image 901B (note that it is variable because the user can move it over different portions of the image 901B) and a variable coordinate with respect to the monitor 900 (note that it is variable because the user can move it all over the monitor 900 including portions of the monitor 900 other than the image 901B). 904 illustrates the y-axis of the monitor coordinate system. In this example (modeled off of the Barco Coronis 5MP, which has an array of 2560×2048 pixels), the y-coordinates of the monitor coordinate system range from 1 to 2560. 905 illustrates the x-axis of the monitor coordinate system. In this example, the x-coordinates of the monitor coordinate system range from 1 to 2048. 906 illustrates the y-axis of the image coordinate system. In this example, the y-coordinates of the image range from 1 to 512. 907 illustrates the x-axis of the image coordinate system. In this example, the x-coordinates of the image range from 1 to 512. Thus, the tumor 902B would have the same first set of image coordinates (as compared to FIG. 1A), but in this example, the tumor would have a second set of monitor coordinates (different from that of FIG. 1A).

Figure 10A:
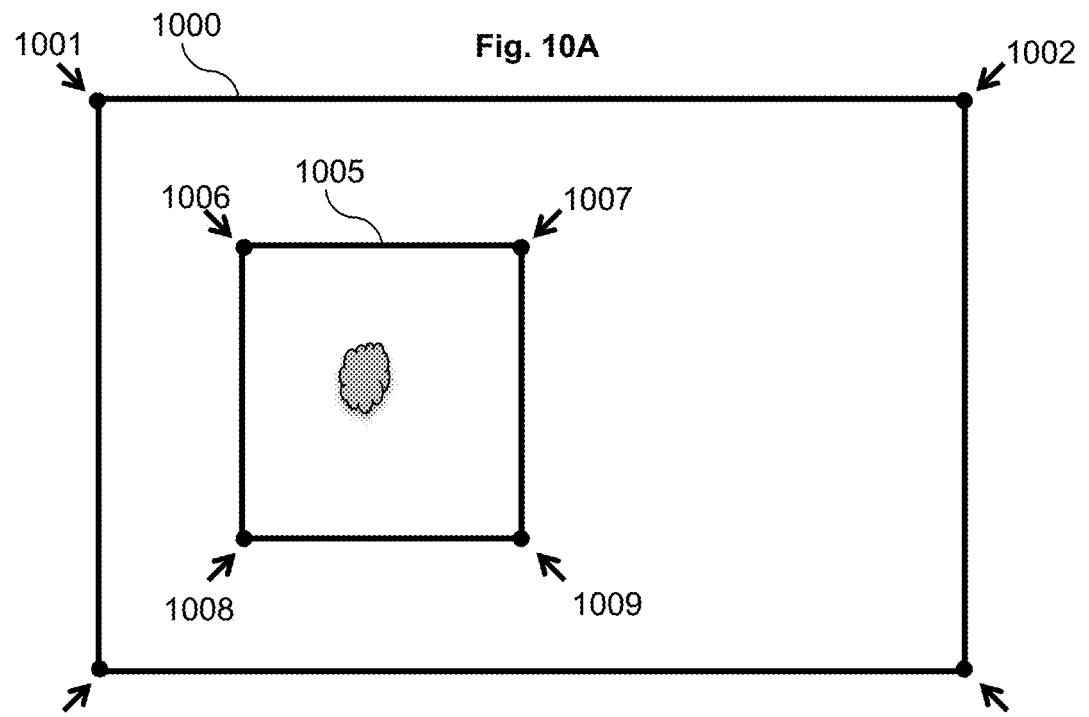
FIG. 10A illustrates the monitor coordinates and first coordinates for an image.

FIG. 10A illustrates the monitor coordinates and first coordinates for an image. 1000 illustrates the monitor. In this example, the monitor has 5200 by 3400 pixels. 1001 illustrates monitor coordinate (1, 3400). 1002 illustrates monitor coordinate (5200, 3400). 1003 illustrates monitor coordinate (1, 1). 1004 illustrates monitor coordinate (5200, 1). 1005 illustrates the image. In this example, the image is sized such that it is displayed as 1500 by 1500 pixels on the monitor 100. 1006 illustrates image coordinate (1, 1500). 1007 illustrates image coordinate (1500, 1500). 1008 illustrates image coordinate (1, 1). 1009 illustrates image coordinate (1500, 1). Note that image coordinate (1, 1) corresponds to monitor coordinate (700, 700).

Figure 10B:
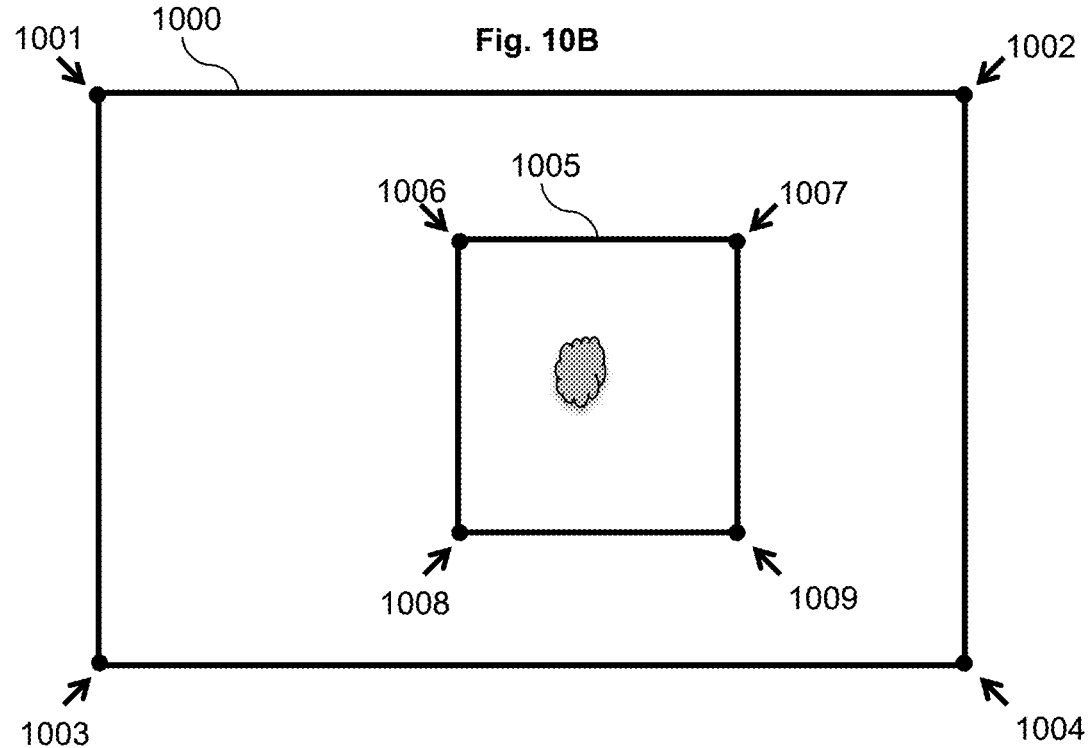
FIG. 10B illustrates the monitor coordinates and second coordinates for an image.

FIG. 10B illustrates the monitor coordinates and second coordinates for an image. 1000 illustrates the monitor. In this example, the monitor has 5200 by 3400 pixels. 1001 illustrates monitor coordinate (1, 3400). 1002 illustrates monitor coordinate (5200, 3400). 1003 illustrates monitor coordinate (1, 1). 1004 illustrates monitor coordinate (5200, 1). 1005 illustrates the image. In this example, the image is sized such that it is displayed as 1500 by 1500 pixels on the monitor 100. 1006 illustrates image coordinate (1, 1500). 1007 illustrates image coordinate (1500, 1500). 1008 illustrates image coordinate (1, 1). 1009 illustrates image coordinate (1500, 1). Note that image coordinate (1, 1) corresponds to monitor coordinate (1800, 700). Note that the image has been translated during a pan function. The preferred embodiment is to have an eye tracking system that determines where the user is looking on the monitor and then determine where the user is looking on the image and then determine which structure (note that the image is segmented into various structures). An alternative embodiment is to track the user's eyes and the image location directly (not specifically track the image location on monitor location).

Figure 11A:
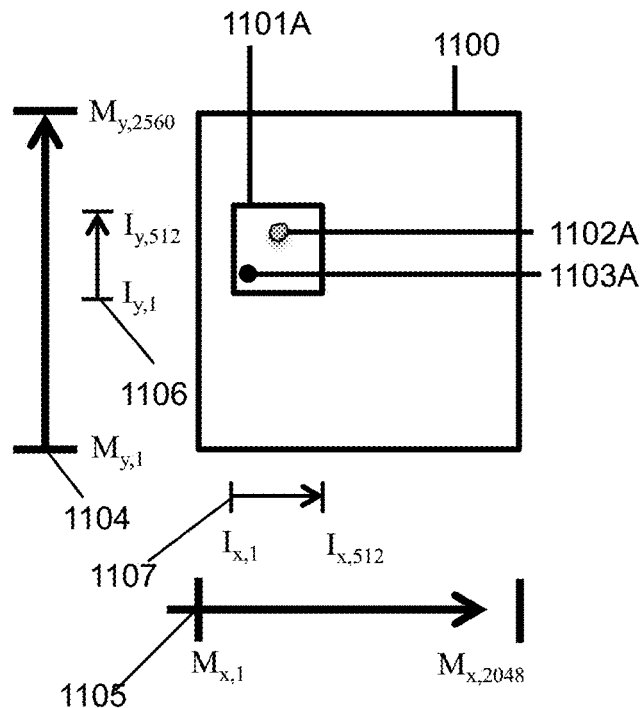
FIG. 11A illustrates an example image of a monitor illustrating the monitor coordinate system and the image coordinate system wherein the image is at a first location and a first zoom status on the monitor.

FIG. 11A illustrates an example image of a monitor illustrating the monitor coordinate system and the image coordinate system wherein the image is at a first location and a first zoom status on the monitor. 1100 illustrates the computer monitor. 1101A illustrates the image on the computer monitor at a first location and first zoom status. Note that it fills up only a small portion of the computer monitor. 1102A illustrates a finding of interest (a tumor) in the image 1101A, which is fixed with respect to the image and a variable coordinate with respect to the monitor (note that it is variable because the user can pan and zoom, which would cause the location of the finding of interest 1102A to move to different locations on the monitor). 1103A illustrates the location of the computer mouse, which has a variable coordinate with respect to the image 1101A (note that it is variable because the user can move it over different portions of the image) and a variable coordinate with respect to the monitor 1100 (note that it is variable because the user can move it all over the monitor 1100 including portions of the monitor 1100 other than the image 1101A). 1104 illustrates the y-axis of the monitor coordinate system. In this example (modeled off of the Barco Coronis 5MP, which has an array of 2560×2048 pixels), the y-coordinates of the monitor coordinate system range from 1 to 2560. 1105 illustrates the x-axis of the monitor coordinate system. In this example, the x-coordinates of the monitor coordinate system range from 1 to 2048. 1106 illustrates the y-axis of the image coordinate system. In this example, the y-coordinates of the image range from 1 to 512. 1107 illustrates the x-axis of the image coordinate system. In this example, the x-coordinates of the image range from 1 to 512. Thus, the tumor 1102A would have a first set of image coordinates and a first set of monitor coordinates. Also, note that the tumor 1102A has a first size (number of pixels on the screen), which is in accordance with the first zoom status.

Figure 11B:
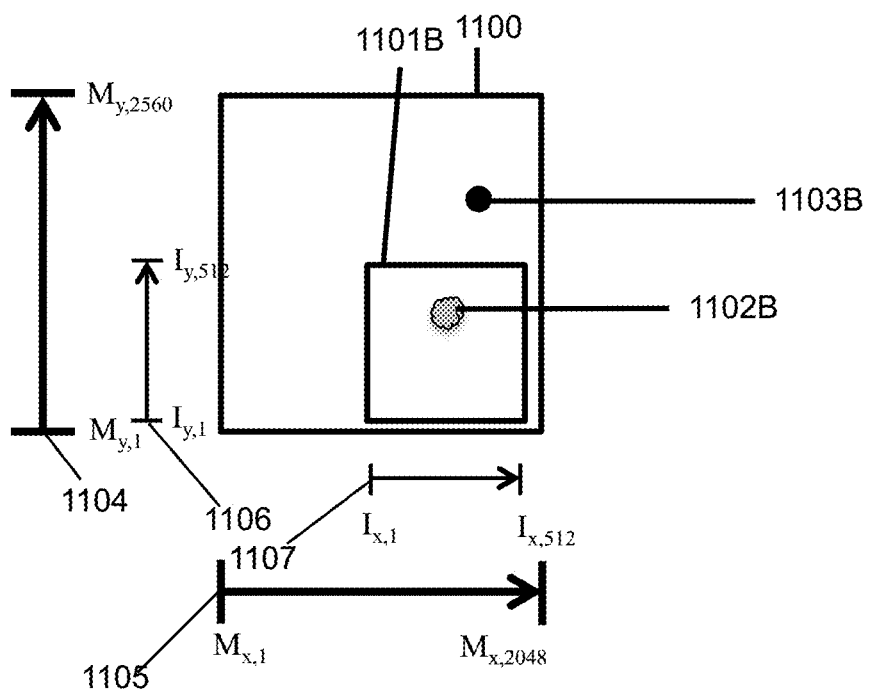
FIG. 11B illustrates an example image of a monitor illustrating the monitor coordinate system and the image coordinate system wherein the image is at a second location and a second zoom status on the monitor.

FIG. 11B illustrates an example image of a monitor illustrating the monitor coordinate system and the image coordinate system wherein the image is at a second location on the monitor. Note that a pan function has been performed wherein the image is moved to a different location on the monitor. This can be performed during maneuvers such to better inspect certain portions of the image. Also, note that the zoom function has been implemented, as indicated by the fact that image 1101B is larger than image 1101A. 1100 illustrates the computer monitor. 1101B illustrates the image on the computer monitor at a second location. Note that it fills up a larger fraction of the computer monitor, as compared to FIG. 11A. 1102B illustrates a finding of interest (a tumor) in the image 1101B, which is fixed with respect to the image 1101B and a variable coordinate with respect to the monitor 1100 (note that it is variable because the user can pan, which would cause the location of the finding of interest 1102B to move to different locations on the monitor 1100). 1103B illustrates the location of the computer mouse, which has a variable coordinate with respect to the image 1101B (note that it is variable because the user can move it over different portions of the image 101B) and a variable coordinate with respect to the monitor 1100 (note that it is variable because the user can move it all over the monitor 1100 including portions of the monitor 1100 other than the image 1101B). In this example, the computer mouse is located on the monitor 1100, but off of the image 1101B. 1104 illustrates the y-axis of the monitor coordinate system. In this example (modeled off of the Barco Coronis 5MP, which has an array of 2560×2048 pixels), the y-coordinates of the monitor coordinate system range from 1 to 2560. 1105 illustrates the x-axis of the monitor coordinate system. In this example, the x-coordinates of the monitor coordinate system range from 1 to 2048. 1106 illustrates the y-axis of the image coordinate system. In this example, the y-coordinates of the image range from 1 to 512. 1107 illustrates the x-axis of the image coordinate system. In this example, the x-coordinates of the image range from 1 to 512. Thus, the tumor 1102B would have the same first set of image coordinates (as compared to FIG. 11A), but in this example, the tumor would have a second set of monitor coordinates (different from that of FIG. 11A).

FIG. 12 illustrates application of the conversion key to convert where a user is looking on a computer monitor to where a user is looking on an image. In this example, a pan procedure is performed. A similar procedure can be performed for zoom. 1200 illustrates a chart for the x-coordinate conversion key with the first column showing time point (in seconds). The second column showing X monitor coordinate and the third column showing the X image coordinate and note that together, these are used to transform the X-coordinate of the eye tracking system on the monitor into the computed X-coordinate of the eye tracking on the image. In the preferred embodiment, the image would be segmented into structures (e.g., anatomic structures such as the radius bone, pathology structures such as a brain aneurysm, and surgical hardware devices). This process enables real time tracking of what the user (e.g., radiologist) is looking at in the image with associated timing metrics including duration and sequence. Recording the monitor coordinate of at least one X data point within an image wherein the at least one data point within an image serves as a reference point for all other data points within the image. A zoom status is also needed to be recorded. 1201 illustrates a chart for the y-coordinate conversion key with the first column showing time point (in seconds). The second column showing Y monitor coordinate and the third column showing the X image coordinate and note that together, these are used to transform the Y-coordinate of the eye tracking system on the monitor into the computed Y-coordinate of the eye tracking on the image. In the preferred embodiment, the image would be segmented into structures (e.g., anatomic structures such as the radius bone, pathology structures such as a brain aneurysm, and surgical hardware devices). This process enables real time tracking of what the user (e.g., radiologist) is looking at in the image with associated timing metrics including duration and sequence. Recording the monitor coordinate of at least one Y data point within an image wherein the at least one data point within an image serves as a reference point for all other data points within the image.

FIG. 13 illustrates generation longitudinal dataset. In this example, a dataset is generated on a user's (e.g., radiologist's) analysis of an examination. A series of variables are recorded at each time point. These variables may include, but are not limited to, the following: time point; a conversion key (i.e., which computer monitor coordinate corresponds to which image coordinate with the associated zoom setting); inputs (if any) by a user (e.g., pan, zoom, window/level, other visual representation adjustment logic); mouse location; and, eye tracking metrics. Note that the eye tracking coordinate on the image can be computed during user inputs such as panning and zooming, as previously described. Eye tracking is performed to determine a user's fixation location on the monitor coordinate system, which in the preferred embodiment is performed at a rapid rate (0.01 second intervals or faster). The monitor-image conversion key is used to determine which fixation location corresponds to which data point within the image (and the associated imaging finding). In some embodiments, an artificial intelligence (AI) algorithm is performed on this newly generated dataset. AI processes can be performed for diagnostic purposes. For example, if eye tracking data shows that a human is looking at a particular spot more times than is typical, then AI processes can be focused in at this spot (or slice). AI processes can also be performed to determine user metrics (e.g., attentiveness, search pattern adequacy, etc.). Additionally, it is important to be able to determine how eye tracking on a first scan correlates to eye tracking on a second scan. For example, consider an adrenal mass imaged in 2019 and 2020. To teach this, it should be noted that the adrenal gland is a deformable tissue (it can change shape over time) and also a movable tissue (it can be moved in position). The same thing is true for other soft structures in the body, such as the kidney. During the 2019 examination, the adrenal gland is flattened from anterior to posterior and is moved (e.g., pushed to the lateral side). During a 2020 examination, the adrenal gland configuration is flattened from medial to lateral and is moved (e.g., pushed to the medial side). Integrating an organ specific coordinate system into eye tracking is therefore useful, as disclosed in U.S. Provisional Patent Application 62/939,685, METHOD AND APPARATUS FOR DEVELOPMENT OF AN ORGAN-SPECIFIC COORDINATE SYSTEM, filed on Nov. 25, 2019, which is incorporated by reference. For example, it would be useful to understand that Radiologist A spent a significant amount of time looking at the medial limb of the left adrenal gland in 2019 because that would clue in Radiologist B who is reading the scan in 2020. The image could be marked (e.g., false color, arrow, circle, other annotations) with the key spots reviewed by a prior radiologist on past examinations. A process to ensure that Radiologist reviews all key areas of concern can also be implemented.

FIG. 14 illustrates a method of altering display settings based on information from eye-tracking technology. In processing block 1400, a list of optimal viewing settings (e.g., predetermined settings) for each item in an image is generated. For example, an example item would be the brain and a predetermined setting for the brain would be a brain window of 30/30. In processing block 1401, the structure that is located at each viewing location (e.g., pixel on 2D monitor or 3D point in space corresponds to liver) is determined. In processing block 1402, an eye-tracker system with an eye-facing camera(s) is initiated. In processing block 1403, eye-movement data with the said eye-facing camera(s) is recorded. In processing block 1404, analysis of the eye-movement data to determine where the user is looking (e.g., the focal point, the fixation point) on the monitor is performed. In processing block 1405, analysis of where the user is looking to determine which item (e.g., brain) the user is examining is performed. In processing block 1406, the current image viewing settings is compared with optimal viewing settings for the particular item in an image being examined to determine whether the viewed object is optimally displayed to the user. Next, the process is illustrated to vary based on whether or not the viewed object is optimally displayed to the user. In processing block 1407, if the viewed object is already optimally displayed to the user, no changes to the image would be performed. In processing block 1408, if the viewed object is not already optimally displayed to the user, viewing settings would be altered such that it is optimally displayed (e.g., smart zoom, smart pan, smart window/level, etc.). Finally, processing block 1409 is to continue eye tracking and optimization of image display settings, as above.

Figure 15:
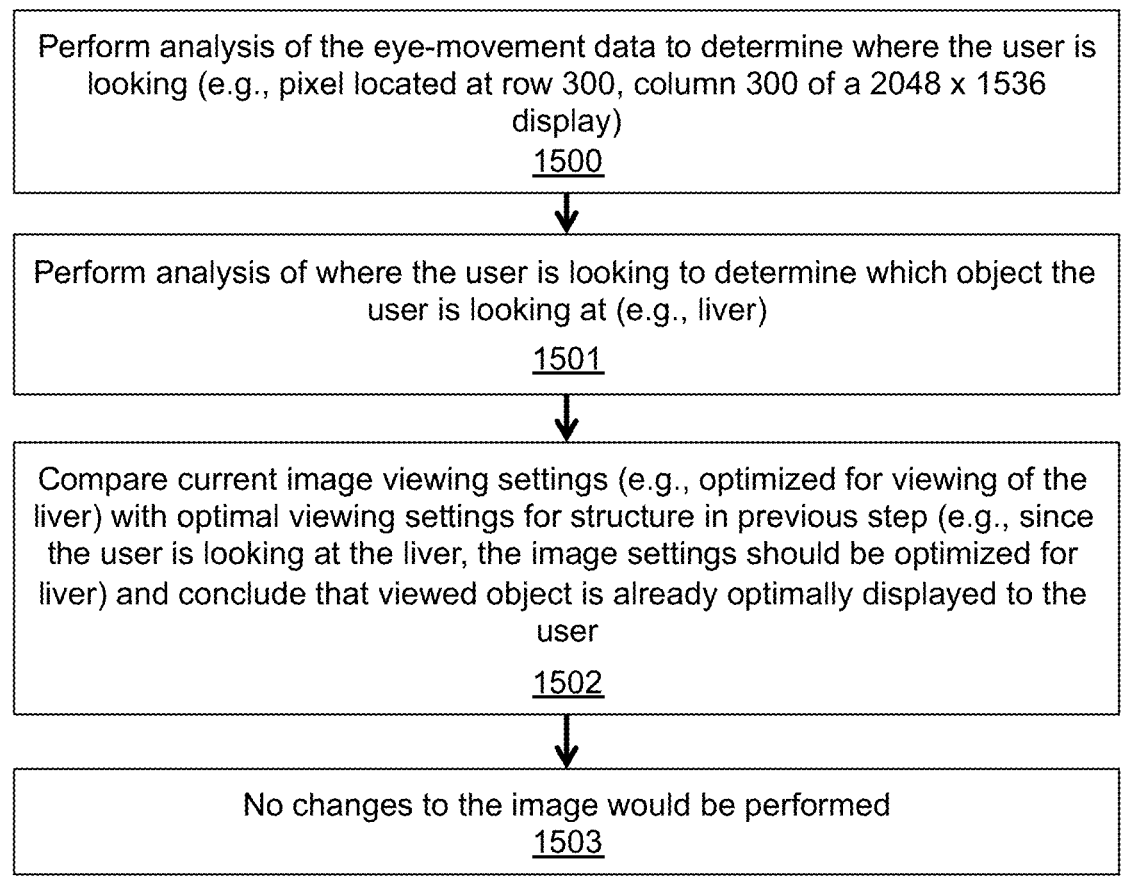
FIG. 15 illustrates an example wherein the spot at which the user is looking already has optimized viewing settings and no changes are made.

FIG. 15 illustrates an example wherein the spot at which the user is looking already has optimized viewing settings and no changes are made. In processing block 1500, analysis of the eye-movement data to determine where the user is looking (e.g., pixel located at row 300, column 300 of the 2048×1536 display) is performed. In processing block 1501, analysis of where the user is looking to determine which object the user is looking at (e.g., liver) is performed. In processing block 1502, the current image viewing settings (e.g., optimized for viewing of the liver) is compared with optimal viewing settings for structure in previous step (e.g., since the user is looking at the liver, the image settings should be optimized for liver) a conclusion is that viewed object is already optimally displayed to the user. In processing block 1503, no changes to the image would be performed. Note that in this example, the example of comparing with optimal viewing settings is illustrated. However, in practice, it could be that a new feature would like to be shown based on where the user is looking. For example, an object would not appear until the eyes look at a certain spot. Alternatively, an object would not disappear until the eyes look at a different spot.

FIG. 16 illustrates an example wherein the spot at which the user is looking is not currently optimized viewing settings and changes to the viewing settings are automatically performed. In processing block 1600, analysis of the eye-movement data to determine where the user is looking (e.g., pixel located at row 600, column 600 of the 2048× 1536 display) is performed. In processing block 1601, analysis of where the user is looking to determine which object the user is looking at (e.g., spleen) is performed. In processing block 1602, the current image viewing settings (e.g., optimized for viewing of the liver) is compared with optimal viewing settings for structure in previous step (e.g., since the user is looking at the spleen, the image settings should be optimized for the spleen) and conclude that viewed object is not currently optimally displayed to the user. In processing block 1603, the image settings from the previous settings (e.g., from being optimized for viewing of the liver) is changed to the new image settings (e.g., being optimized for the spleen).

Figure 17A:
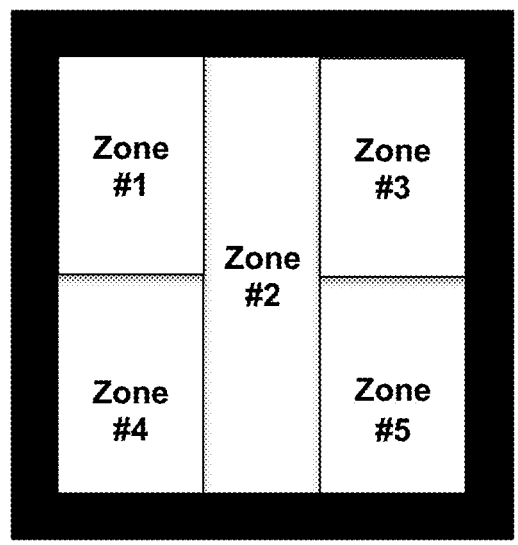
FIG. 17A illustrates assigning zones wherein when a user looks at a particular zone, a corresponding image manipulation occurs.
Figure 17B:
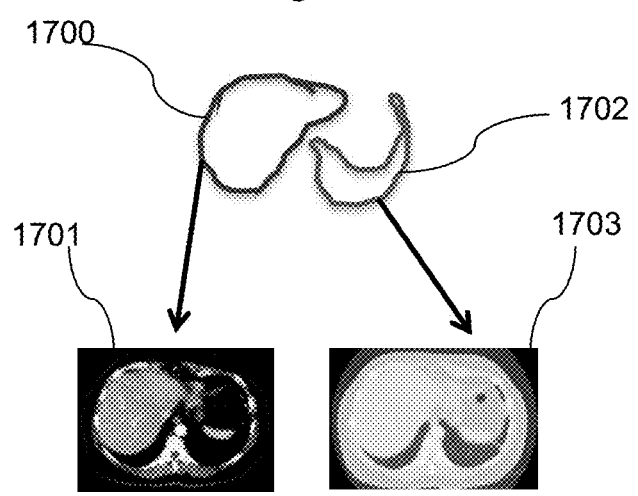
FIG. 17B illustrates dividing up the field of view into regions based on segmentation.

FIG. 17A illustrates assigning zones wherein when a user looks at a particular zone, a corresponding image manipulation occurs. Note that in this embodiment, the zones which are rectangle shaped would not perfectly correspond to the anatomic structures of the human body, which are not rectangle shaped. This boundary is meant to approximate the regions of a CT chest examination in the coronal plane at the posterior third of the chest. This is a simplified segmentation algorithm meant to serve as a first approximation, which will be followed by more precise boundaries, as shown in FIG. 17B. For example, the radiologist may prefer to have the lung display settings be displayed anytime that he/she is looking at the top left (i.e., Zone #1) of the monitor for the display settings to be optimized for lung. If his/her eyes ever so slightly gazed over to the fat within the chest wall, he/she may prefer to still have the settings be optimized for lung and would not want it to change to an optimized setting for viewing fat. Similarly, the radiologist can look at Zone #2 and have image settings optimized for the bone. Similarly, the radiologist can look at Zone #3 and have image settings optimized for the lung. Similarly, the radiologist can look at Zone #4 and have imaging settings optimized for the liver. Similarly, the radiologist can look at Zone #5 and have imaging settings optimized for the spleen. Thus, a map of pixel location and preferred viewing settings would be established per user preference. Note that in the preferred embodiment, a 3D pixel map would be generated. For each viewing location (e.g., pixel on 2D monitor), determine the structure that is located at that point (or in that region) and then optimize the image for the anatomic structure in that region. A double windowing technique may be used in conjunction with this, as described in U.S. Pat. No. 10,586, 400. This will help prevent some errors. For example, sometimes a radiologist is looking and examining bone for quite some time yet the window/level settings are optimized for soft tissue and could miss a finding as a result. This system would resolve this potential source of error.

FIG. 17B illustrates dividing up the field of view into regions based on segmentation. This method of dividing may be more closely aligned with segmentation algorithms. For example, if the user is looking at the area defined by the liver region 1700, then a liver window is displayed as shown in 1701. If the user is looking at the area defined by the right lung base 1702, then a lung window is displayed as shown in 1703. A double windowing technique may be used in conjunction with this, as described in U.S. Pat. No. 10,586, 400, PROCESSING 3D MEDICAL IMAGES TO ENHANCE VISUALIZATION, which is incorporated by reference. In addition, the zones could be determined by methods described in U.S. patent application Ser. No. 16/785,606, IMPROVING IMAGE PROCESSING VIA A MODIFIED SEGMENTED STRUCTURE, which is incorporated by reference.

FIG. 18 illustrates generating a list of the optimal viewing settings for each item in an image. 1800 illustrates a chart showing two items within an image are shown along with the optimal viewing settings during 2D slice-by-slice viewing per user preference. For example, liver could be shaded as a rainbow color scheme to bring out subtle lesions. All other tissues in the image slice are turned to dark gray shades, which will provide context. For example, bone is colored ranging from medium gray to very light gray shades (per user preference). All other tissues are turned to dark gray shades, which will provide continued context. 1801 illustrates a chart showing two items within an image are shown along with the optimal viewing settings during 3D augmented reality volume-by-volume viewing per user preference. For example, bands-wise prioritization of HU ranges is utilized within the liver and displayed in a dynamic fashion to make more subtle (but dangerous lesions) easier to detect. To perform this, the voxels that subtend the liver are divided into bands based on their property (e.g., Hounsfield Unit). For example, assume that voxels that subtend the liver have Hounsfield of 30-60. These can be divided into 3 bands (e.g., upper range of 50-60 HU, a middle range of 40-50 HU, and a lower range of 30-40 HU) wherein at three different time points one of the bands has enhanced visualization (e.g., grayscale) and the other two bands have diminished visualization (e.g., black). This process wherein voxels are divided into bands and then visualization enhanced or diminished improves detection of subtle lesions. All other tissues are made more translucent (e.g., sparse sampling) or are filtered. For example, for bone prioritized volume rendering (U.S. patent Ser. No. 16/842, 631) is performed wherein the bone surface is displayed unless the is a lesion within the central aspect of the bone, which would then be higher priority and be displayed. All other tissues are made more translucent (e.g., sparse sampling) or are filtered. This is more thoroughly described in U.S. Pat. No. 10,586,400, the figures and detailed description.

Figure 19A:
FIG. 19A illustrates an image optimized for visualization of abdominal organs.

FIG. 19A illustrates an image optimized for visualization of abdominal organs. 1900 illustrates a CT slice where the entire CT slice is displayed with a single window/level setting.

Figure 19B:
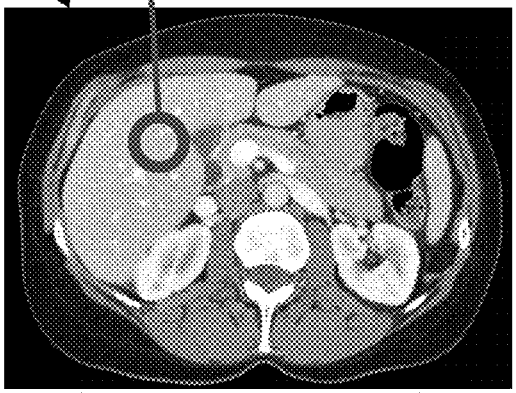
FIG. 19B illustrates an image optimized for visualization of abdominal organs with a fixation point.

FIG. 19B illustrates an image optimized for visualization of abdominal organs with a fixation point. 1900 illustrates a CT slice where the entire CT slice is displayed with a single window/level setting. 1901 illustrates a first fixation point (determined by the eye tracking system), which is located on the liver.

Figure 19C:
FIG. 19C illustrates an image, which has been altered due to a prior fixation point.

FIG. 19C illustrates an image, which has been altered due to a prior fixation point. 1902 illustrates a CT slice where a portion of the image has been altered (darkened in this example) to indicate that it has been reviewed. The area darkened can be determined by user preference. 1903 illustrates the darkened portion of the image from the first fixation point. Note that the remaining portions of the image are shown with normal brightness, as in FIGS. 19A and 19B.

Figure 19D:
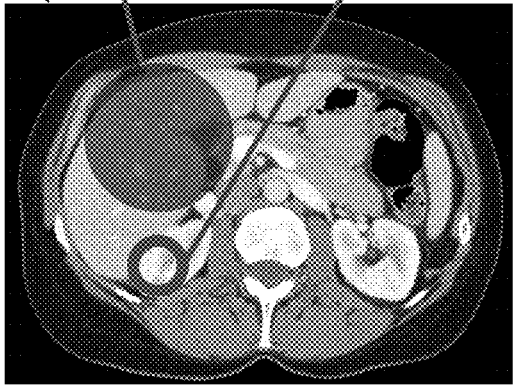
FIG. 19D illustrates an image, which is partially darkened with a second fixation point shown.

FIG. 19D illustrates an image, which is partially darkened with a second fixation point shown. 1902 illustrates a CT slice where a portion of the image has been altered (darkened in this example) to indicate that it has been reviewed. 1903 illustrates the darkened portion of the image. Note that the remaining portions of the image are shown with normal brightness, as in FIGS. 19A and 19B. 1904 illustrates a second fixation point, which is shown on the right kidney.

Figure 19E:
FIG. 19E illustrates an image, which is partially darkened at the locations of the two prior fixation points.

FIG. 19E illustrates an image, which is partially darkened at the locations of the two prior fixation points. 1905 illustrates a CT slice where a portion of the image has been altered (darkened in this example) to indicate that it has been reviewed. 1903 illustrates the darkened portion of the image from the first fixation point. 1906 illustrates the darkened portion of the image from the second fixation point.

Figure 19F:
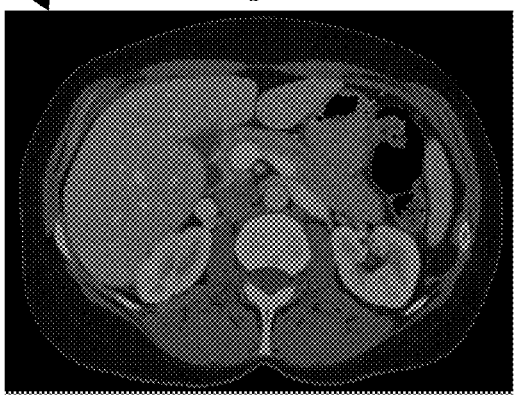
FIG. 19F illustrates an image, which is completely darkened, which occurs when a slice is fully inspected.

FIG. 19F illustrates an image, which is completely darkened, which occurs when a slice is fully inspected. 1907 illustrates a CT slice fully darkened, which indicates that is has been completely reviewed. Thus, this embodiment provides a process of changing the appearance of an image based on eye tracking. The visual appearance can change in terms of brightness (darkening vs. brightening), contrast (sharp vs. blurred), timing of display (during inspection vs after inspection), rate of display of the new visual appearance (rapid display of new image vs fading in of new image over time). Note that the darkening can be shown over multiple time steps (in accordance with the fixation points) or the user could be allowed a period of time (e.g., 4.0 seconds) and then all areas closely inspected with fixation points darkened and all areas not closely inspected with fixation points shown in normal brightness fashion. Furthermore, areas that are not reviewed could be flagged to the user. Overall, these processes improves image analysis by alerting to the reviewer which areas have been inspected and which areas have not been inspected. Furthermore, in some embodiments, areas actively under inspection could be given an first visual representation adjustment logic. Areas that have been previously inspected could be given a second visual representation adjustment logic. Areas that have not been inspected could be given a third visual representation adjustment logic.

FIG. 20 illustrates an example of changing of the appearance of an image in accordance with eye tracking. 2000 illustrates a processing block of displaying an image with a first example set of parameters (e.g., soft tissue window). An example includes a CT slice through the abdomen with a standard window and level setting (e.g., soft tissue window). 2001 illustrates a processing block of moving to a segmented item to be analyzed (e.g., via eye tracking is performed and it is determined that the user is closely inspecting the pancreas, etc.). The pancreas therefore acts as a triggering spot. 2002 illustrates a processing block of adjusting display settings (e.g., window and leveling) of an item (e.g., pancreas) to be analyzed to optimize viewing of the item and option to also adjust display settings of segmented items not currently being analyzed. In this example, the double windowing technique described in U.S. Pat. No. 10,586,400, PROCESSING 3D MEDICAL IMAGES TO ENHANCE VISUALIZATION, was performed, which allows improved visual appearance of the pancreas. An alteration of the appearance of an image based on eye tracking and where the user is looking at on the image is performed. In this example, dual windowing is shown wherein a first portion of the image (i.e., pancreas) is shown with optimum window and level setting and the remainder of the image is shown with bone window/level setting. This serves to bring the user's attention to the pancreas. Other techniques, such as halo windowing can also be incorporated. In addition, with regards to changing display settings, if the user is looking at the vertebral body for more then 1.00 seconds, the visual representation can be set to automatically change to optimize viewing of the vertebral body (e.g., optimize gray scale appearance of the vertebral body and make all other structures in the field of view darkened). A wide range of visual representation adjustment logic schemes are anticipated to be performed in response to eye tracking metrics. First, techniques include voxel filtering and stereoscopic rendering and others are incorporated as described by U.S. Pat. No. 8,384,771, METHOD AND APPARATUS FOR THREE DIMENSIONAL VIEWING OF IMAGES, which is incorporated by reference. Next, techniques include convergence and others are incorporated as described by U.S. Pat. No. 9,349,183, METHOD AND APPARATUS FOR THREE DIMENSIONAL VIEWING OF IMAGES, which is incorporated by reference. Next, techniques include the use of alternative head display units and others are incorporated as described by U.S. Pat. No. 9,473,766, METHOD AND APPARATUS FOR THREE DIMENSIONAL VIEWING OF IMAGES, which is incorporated by reference. Next, techniques include the use of a 3D volume cursor and others are incorporated as described by U.S. Pat. No. 9,980,691, METHOD AND APPARATUS FOR THREE DIMENSIONAL VIEWING OF IMAGES, which is incorporated by reference. Next, techniques include the use of an interactive 3D cursor and others are incorporated as described by U.S. patent application Ser. No. 15/878,463, INTERACTIVE 3D CURSOR FOR USE IN MEDICAL IMAGING, which is incorporated by reference. Next, techniques include double windowing and others are incorporated and others as described in U.S. Pat. No. 10,586, 400, PROCESSING 3D MEDICAL IMAGES TO ENHANCE VISUALIZATION, which is incorporated by reference. Next, techniques including use of modified segmented structure and others are incorporated as described in U.S. patent application Ser. No. 16/785,606, IMPROVING IMAGE PROCESSING VIA A MODIFIED SEGMENTED STRUCTURE, which is incorporated by reference. Next, techniques including use of double compression mammography and others are incorporated as described in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference. Next, techniques including those of smart scrolling and others are incorporated as described in U.S. patent application Ser. No. 16/842,631, A SMART SCROLLING SYSTEM, which is incorporated by reference. Next, techniques of eye tracking are incorporated as disclosed in U.S. Provisional Patent Applications 62/856,185 filed on Jun. 3, 2019 and 62/985, 363 filed on Mar. 5, 1920, which are incorporated by reference. Next, techniques of affixing a sub-volume onto a geo-registered tool are incorporated as disclosed in U.S. Pat. No. 10,712,837, USING GEO-REGISTERED TOOLS TO MANIPULATE THREE-DIMENSIONAL MEDICAL IMAGES, which is incorporated by reference. Next, techniques of virtual toolkit and others are incorporated as disclosed in PCT/US2019/036904, A VIRTUAL TOOL KIT FOR 3D IMAGING, which is incorporated by reference. Next, techniques of interaction between geo-registered tools and virtual tools are incorporated as disclosed in U.S. patent application Ser. No. 16/563,985, A METHOD AND APPARATUS FOR THE INTERACTION OF VIRTUAL TOOLS AND GEO-REGISTERED TOOLS, which is incorporated by reference. Next, techniques of prioritized volume rendering are incorporated as disclosed in U.S. patent application Ser. No. 16/879,758, A METHOD AND APPARATUS FOR PRIORITIZED VOLUME RENDERING, which is incorporated by reference. Next, techniques of radiologist assisted machine learning are incorporated as disclosed in PCT/US2019/023968, RADIOLOGIST-ASSISTED MACHINE LEARNING WITH INTERACTIVE, VOLUME-SUBTENDING 3D CURSOR, which is incorporated by reference. Next, techniques of illustrating flow are incorporated as disclosed in U.S. patent application Ser. No. 16/506,073, A METHOD FOR ILLUSTRATING DIRECTION OF BLOOD FLOW VIA POINTERS, and Ser. No. 16/779,658, 3D IMAGING OF VIRTUAL FLUIDS AND VIRTUAL SOUNDS, which are incorporated by reference. Next, techniques of sub-volume isolation and targeting are incorporated as disclosed in U.S. patent application Ser. No. 16/927,886, A METHOD AND APPARATUS FOR GENERATING A PRECISION SUB-VOLUME WITHIN THREE-DIMENSIONAL IMAGE DATASETS, which is incorporated by reference.

Figure 21:
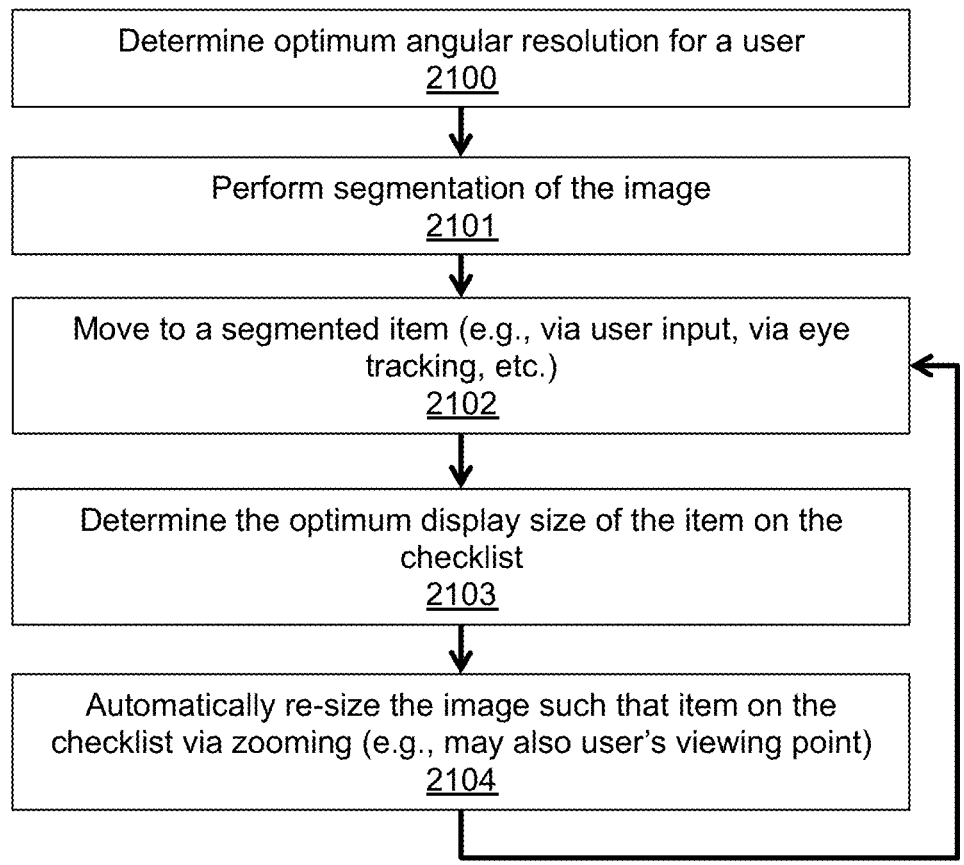
FIG. 21 illustrates a smart zoom process.

FIG. 21 illustrates a smart zoom process. 2100 illustrates a processing block of determining the optimum angular resolution for a user. 2101 illustrates a processing block of performing segmentation of the image. 2102 illustrates a processing block of moving to a segmented item (e.g., via user input, via eye tracking, etc.). 2103 illustrates a processing block of determining the optimum display size of the item on the checklist. 2104 illustrates a processing block of automatically re-size the image such that item on the checklist via zooming (e.g., may also user's viewing point). Subsequently, return to processing block 2102.

FIG. 22A illustrates an imaging finding displayed on a monitor. 2200 illustrates a point between the eyes. 2201 illustrates the monitor. $\alpha_1$ illustrates the angular resolution that object $D_1$ appears on the screen. $L_1$ illustrates the distance from the point between the eyes 2200 to the monitor 2201. Assume a 30 inch monitor. Assume viewing distance of 24 in. Assume an adrenal gland shows up at a 0.5 inch item on the screen under a first viewing setting. The angular resolution of the adrenal gland would be approximately 1.2 degrees.

FIG. 22B illustrates an imaging finding displayed on a monitor. 2200 illustrates a point between the eyes. 2201 illustrates the monitor. $\alpha_2$ illustrates the angular resolution that object $D_2$ appears on the screen. $L_2$ illustrates the distance from the point between the eyes 2200 to the monitor 2201. Assume a 30 inch monitor. Assume viewing distance of 24 in. Assume that the optimum angular resolution of the adrenal gland is 2.4 degrees. Once implemented (e.g., via moving to the adrenal gland item on the checklist or via eye tracking wherein the user looks at the adrenal gland for some pre-specified time period such as 1.00 seconds), the adrenal gland is enlarged on the monitor up to a size of 1.0 inch. This enlargement can occur in an instant (over a single frame) or via gradual enlargement (over several frames). The "smart zoom" function enlarges the size of the adrenal gland on the screen to the desired level (e.g., 2 degrees, 3 degrees, etc.). This can improve image detection and analysis. In this embodiment, a smart zoom process is initiated. Some anatomic structures, such at the adrenal gland, are relatively small. Small nodules, such as adrenal adenomas, would be better detected if the adrenal glands were displayed on the radiology monitor in an enlarged fashion. The preferred method for a smart zoom process comprises showing an anatomic feature at a size on the monitor, which is optimized for the user. A user's fovea has the optimum visual acuity and is typically approximately 2 degrees. There would be little utility to show a structure smaller than 2 degrees and the user's high resolution visual acuity would not be fully used. As the distance away from the fovea increased the visual acuity drops. Thus, for some anatomic features (e.g., adrenal gland) wherein very close inspection is necessary, a smart zoom automatically sizes the anatomic feature (e.g., adrenal gland) appropriately. For example, the adrenal gland can take on the appropriate size on the monitor that the anatomic structure appears 2× the fovea field of view or approximately 4 degrees. Note that the typical state of the right adrenal gland. In some embodiments, the smart zoom would automatically size an anatomic feature on the image for 1.5× the fovea field of view, which would be 3 degrees. In some embodiments, the smart zoom would automatically size an anatomic feature on the image for 2× the fovea field of view, which would be 4 degrees. In some embodiments, the smart zoom would automatically size an anatomic feature on the image for 3× the fovea field of view, which would be 6 degrees. In some embodiments, the smart zoom would automatically size an anatomic feature on the image for a user-specified multiplier of the fovea field of view. And so on. The preferred embodiment of this process is to performed smart zoom in conjunction with a radiologist's checklist. For example, the radiologist's first item on an abdominal CT scan checklist is the liver. In accordance with the pre-determined optimal zoom status, the liver is at 7.5× the fovea field of view, which would be 15 degrees. The CT scan slices of the liver are shown to the user in a first zoom state wherein the liver comprises 15 degrees of the user's field of view. Once the radiologist has completed the liver item on the checklist, the radiologist moves to the gallbladder, which is the second item on the checklist. In accordance with the pre-determined optimal zoom status, the gallbladder is at 2× the fovea field of view, which would be 4 degrees. The CT scan slices of the gallbladder are shown to the user in a second zoom state wherein the gallbladder comprises 4 degrees of the user's field of view. Once the radiologist has completed the gallbladder item on the checklist, the radiologist moves to the spleen, which is the third item on the checklist. In accordance with the pre-determined optimal zoom status, the spleen is at 4x the fovea field of view, which would be 8 degrees. The CT scan slices of the spleen are shown to the user in a third zoom state wherein the spleen comprises 4 degrees of the user's field of view. Once the radiologist has completed the spleen item on the checklist, the radiologist moves to the pancreas, which is the fourth item on the checklist. In accordance with the pre-determined optimal zoom status, the pancreas is at 3.5× the fovea field of view, which would be 7 degrees. The CT scan slices of the pancreas are shown to the user in a fourth zoom state wherein the pancreas comprises 7 degrees of the user's field of view. Once the radiologist has completed the pancreas item on the checklist, the radiologist moves to the right adrenal gland, which is the fifth item on the checklist. In accordance with the pre-determined optimal zoom status, the right adrenal gland is at 2× the fovea field of view, which would be 4 degrees. The CT scan slices of the right adrenal gland are shown to the user in a fifth zoom state wherein the right adrenal gland comprises 4 degrees of the user's field of view.

FIG. 23A illustrates determining and recording which areas (e.g., voxels or pixels) are included in the high resolution FOV, which areas (e.g., voxels or pixels) are included in the medium resolution FOV, and which areas (e.g., voxels or pixels) are included in the low resolution FOV. A table is illustrates to show data that can also be collected in a longitudinal fashion. In this embodiment, three sets of voxels are included at each time point. During time point 0.01 seconds, set A of voxels would be recorded in the high resolution field of view, set B of voxels would be recorded in the medium resolution field of view, and set C of voxels would be recorded in the low resolution field of view. During time point 0.02 seconds, set D of voxels would be recorded in the high resolution field of view, set E of voxels would be recorded in the medium resolution field of view, and set F of voxels would be recorded in the low resolution field of view. During time point 0.03 seconds, set G of voxels would be recorded in the high resolution field of view, set H of voxels would be recorded in the medium resolution field of view, and set I of voxels would be recorded in the low resolution field of view. During time point 0.04 seconds, set J of voxels would be recorded in the high resolution field of view, set K of voxels would be recorded in the medium resolution field of view, and set L of voxels would be recorded in the low resolution field of view.

FIG. 23B illustrates a zoomed in 8×8 set of voxels, showing assigning some voxels to a high resolution FOV and some voxels to a medium resolution FOV in accordance with FIG. 23A. A total of 24 voxels are illustrated in Set A in this example. Set B would contain an additional 40 voxels in this example. Voxels assigned to Set C are not shown in this Figure. The voxels could be stored by their (x, y, z locations). This would be useful because it would allow a more precise way of determining how well the 3D dataset has been reviewed. Furthermore, it is useful because voxel located at data point at the x, y, z coordinate (150, 200, 250) could be tracked at which time points it is viewed during the examination. Furthermore, voxels that are marked as abnormal by an AI algorithm could also be tracked and determined how well these areas have been reviewed by a human (e.g., radiologist).

FIG. 24 illustrates a method of generating metrics based on which imaging features have been reviewed. Processing block 2400 determines metrics (e.g., imaging features thoroughly viewed, imaging features not examined). Processing block 2401 displays an imaging dataset on a computer monitor. Processing block 2402 performs segmentation of the imaging dataset (e.g., segment a brain MRI into the frontal lobe, temporal lobe, pituitary gland, etc.). Processing block 2403 determines the location(s) of imaging features on the monitor (e.g., performed in a dynamic fashion wherein an imaging finding may change in position over time during zooming or panning by a user). Processing block 2404 tracks eye movements of a user to determine the fixation locations at pixels on the monitor and the corresponding imaging features being viewed. Processing block 2405 records data on fixation locations and discrete imaging features (e.g., sequence of viewing of imaging features, length of time an imaging feature has been viewed, etc.). Processing block 2406 analyzes the recorded data on fixation locations and discrete imaging features. Processing block 2407 reports metrics to the user. Processing block 2408 alters imaging display based on metrics above (e.g., make imaging features not sufficiently viewed based on predetermined standards stand out in such a way as to draw the user's attention).

FIG. 25 illustrates assigning a set of predetermined locations within an image that should be viewed by a user in order for a comprehensive review to be performed. 2500 illustrates a processing block of performing eye-tracking with an eye-facing camera to determine a set of fixation locations in the monitor. 2501 illustrates a processing block of correlating the fixation locations to their corresponding imaging features. 2502 illustrates a processing block of determining which predetermined locations have been viewed and which predetermined locations have not been viewed. 2503 illustrates a processing block of alerting user of those predetermined locations which have not been viewed. A first example is providing a visual alert cue adjacent to those predetermined locations which have not been viewed. A second example is providing a first visual representation adjustment logic for the pixels nearby the predetermined locations which have been viewed and a second visual representation adjustment logic for those pixels nearby the predetermined locations which have not been viewed.

FIG. 26 illustrates comparing the analyzed recorded data on fixation locations and discrete imaging features with a predetermined criteria of minimum imaging metrics that must be met for a complete review. Processing block 2600 illustrates a text box of example criteria a minimum number of fixation locations for the imaging dataset. These criteria include: a minimum number of fixation locations for each imaging feature (e.g., 5 fixation locations within 10 mm of the central point of the pituitary gland); a minimum number of fixation locations for each subsegmented spot (e.g., frontal lobe) within an imaging feature (e.g., brain); a minimum length of fixation location for each imaging feature (e.g., 50 fixation locations for the liver); a minimum number of imaging planes an imaging feature has fixation locations in situations comprising wherein the imaging dataset comprises cross-sectional imaging planes (e.g., fixation locations on 3 plans for the pituitary gland, fixation locations on two planes for the corpus callosum, etc.); whether or not the imaging structure had optimized display during a fixation location (e.g., a fixation location on the vertebral body is considered adequate if the vertebral body is windowed so that the vertebral body is optimized whereas a fixation location on the vertebral body is not considered adequate if the vertebral body is not windowed so that the vertebral body is optimized); and, whether or not a predetermined sequence of fixation locations for each imaging feature has been achieved (e.g., predetermined sequence would be aortic arch, lower common carotid artery, middle common carotid artery, upper common carotid artery, lower internal carotid artery, middle internal carotid artery and upper internal carotid artery, which shows that a methodical search was performed. Random points along the carotid artery may not indicate as comprehensive of a search.). Processing block 2601 illustrates a text box of altering the displayed image based on the relationship between the analyzed data and the predetermined threshold. Processing block 2602 illustrates a text box of altering the brightness of imaging feature(s) that have met the predetermined threshold wherein the imaging feature(s) that have met the predetermined threshold are assigned a first visual representation adjustment logic. Processing block 2603 illustrates a text box of altering the brightness of imaging feature(s) that have not met the predetermined threshold wherein the imaging feature(s) that have not met the predetermined threshold are assigned a second visual representation adjustment logic.

What is claimed is:

1. A method comprising:
for a first time epoch, performing the steps comprising:
displaying an image onto a display with a first set of display settings;
using an eye facing camera to track a user's first fixation location on the display;
determining a first imaging finding located at the user's first fixation location on the display;
recording data in a dataset including the first imaging finding with a first set of display settings;
for a subsequent time epoch, performing the steps comprising:
displaying the image with a subsequent set of display settings
wherein the subsequent set of display settings is different from the first set of display settings;
using the eye facing camera to track the user's subsequent fixation location on the display;
determining a subsequent imaging finding located at the user's subsequent fixation location on the display
wherein the subsequent imaging finding comprises a segmented item,
wherein the segmented item is assigned an optimal viewing setting, and
wherein the subsequent fixation location at the subsequent imaging finding causes the subsequent imaging finding to be displayed with said optimal viewing setting; and
recording data in the dataset including the subsequent imaging finding with the subsequent set of display settings.

2. The method of claim 1 further comprising analyzing the dataset to determine the extent of the review by the user.

3. The method of claim 1 further comprising analyzing the dataset comprising generating metrics correlating fixation locations with imaging findings comprises of at least one of the group consisting of:
a number of fixation location(s) for an imaging finding;
an imaging plane of fixation location(s) for an imaging finding; and
a sequence of fixation location(s) for an imaging finding.

4. The method of claim 3 further comprising determining an average for each metric for the user and providing an notification to the user when a current exam's metric differs from the average.

5. The method of claim 3 further comprising determining an average for each metric for a population of users to develop a set of normative metrics and providing a notification to the user when the user's metric differs from the population.

6. The method of claim 1 further comprising comparing the dataset with a predetermined criteria to determine whether a minimum review has been completed wherein the predetermined criteria comprises of at least one of the group consisting of:
a minimum number of fixation locations for the image;
a minimum number of fixation locations for each imaging finding;
a minimum number of fixation locations for each subsegmented area within an imaging finding;
a minimum viewing time for each imaging feature;
a minimum number of imaging planes an imaging finding has fixation locations in situations comprising wherein the imaging dataset comprises cross-sectional imaging planes;
a determination of whether or not a structure had optimized display during a fixation location; and
a determination of whether or not a predetermined sequence of fixation locations for each imaging feature has been achieved.

7. The method of claim 6 further comprising altering the displayed image based on the relationship between the analyzed dataset and the predetermined criteria further comprising:
assigning a first visual representation adjustment logic to imaging finding(s) that have met the predetermined criteria; and
assigning a second visual representation adjustment logic to imaging finding(s) that have not met the predetermined criteria wherein the first visual representation adjustment logic is different from the second visual representation adjustment logic.

8. The method of claim 7 further comprising providing visual feedback to the user based on whether or not the predetermined criteria has been met to guide the user in the performance of a comprehensive review of the image.

9. The method of claim 1 further comprising wherein the display has a curvature comprising:
the top portion of the monitor curves inwards towards the user;
the bottom portion of the monitor curves inwards towards the user;
the left portion of the monitor curves inward towards the user; and
the right portion of the monitor curves inward towards the user.

10. The method of claim 1 further comprising utilizing a head display unit (HDU) comprising of at least one of the group consisting of: an extended reality display; eye display with shutters; and, eye display with polarized lenses.

11. The method of claim 1 further comprising using a keyboard comprising wherein the center of the keyboard is in an elevated position with respect to the sides of the keyboard.

12. The method of claim 1 further comprising wherein the display setting comprises at least one of the group consisting of: a pan setting; a zoom setting; and, a window/level setting.

13. The method of claim 1 further wherein the dataset comprises data on areas of the image included in the user's high resolution field of view.

14. The method of claim 1 further comprising using eye tracking data to implement at least one of the group comprising: a smart panning viewing option; a smart zoom viewing option; and a smart window/level viewing option.

15. The method of claim 1 further comprising analyzing the dataset by an artificial intelligence algorithm.

16. A non-transitory computer readable medium having computer readable code thereon for image processing, the medium comprising:
instructions for a first time epoch, performing the steps comprising:
displaying an image onto a display with a first set of display settings;
using an eye facing camera to track a user's first fixation location on the display;
determining a first imaging finding located at the user's first fixation location on the display;

recording data in a dataset including the first imaging finding with a first set of display settings;
instructions for a subsequent time epoch, performing the steps comprising:
  displaying the image with a subsequent set of display settings wherein the subsequent set of display settings is different from the first set of display settings;
  using the eye facing camera to track the user's subsequent fixation location on the display;
  determining a subsequent imaging finding located at the user's subsequent fixation location on the display; and
  recording data in the dataset including the subsequent imaging finding with the subsequent set of display settings;
instructions that compare the dataset with a predetermined criteria to determine whether a minimum review has been completed wherein the predetermined criteria comprises of at least one of the group consisting of:
a minimum number of fixation locations for the image;
a minimum number of fixation locations for each imaging finding;
a minimum number of fixation locations for each subsegmented area within an imaging finding;
a minimum viewing time for each imaging finding;
a minimum number of imaging planes an imaging finding has fixation locations in situations comprising wherein the imaging dataset comprises cross-sectional imaging planes;
a determination of whether or not a structure had optimized display during a fixation location; and
a determination of whether or not a predetermined sequence of fixation locations for each imaging feature has been achieved,
instructions that alter the displayed image based on the relationship between the analyzed dataset and the predetermined criteria further comprising:
  assigning a first visual representation adjustment logic to imaging finding(s) that have met the predetermined criteria; and
  assigning a second visual representation adjustment logic to imaging finding(s) that have not met the predetermined criteria where the first visual representation adjustment logic is different from the second visual representation adjustment logic; and
instructions that provide visual feedback to the user based on whether or not the predetermined criteria has been met to guide the user in the performance of a comprehensive review of the image.

17. A computer system comprising:
a memory;
a processor; and wherein the memory is encoded with an application providing image processing that when performed on the processor provides a process for processing information, the process causing the computer system to perform the operations of:
for a first time epoch, performing the steps comprising:
  displaying an image onto a display with a first set of display settings;
  using an eye facing camera to track a user's first fixation location on the display;
  determining a first imaging finding located at the user's first fixation location on the display;
  recording data in a dataset including the first imaging finding with a first set of display settings;
for a subsequent time epoch, performing the steps comprising:
  displaying the image with a subsequent set of display settings wherein the subsequent set of display settings is different from the first set of display settings;
  using the eye facing camera to track the user's subsequent fixation location on the display;
  determining a subsequent imaging finding located at the user's subsequent fixation location on the display; and
  recording data in the dataset including the subsequent imaging finding with the subsequent set of display settings
comparing the dataset with a predetermined criteria to determine whether a minimum review has been completed wherein the predetermined criteria comprises of at least one of the group consisting of,
  a minimum number of fixation locations for the image;
  a minimum number of fixation locations for each imaging finding;
  a minimum number of fixation locations for each subsegmented area within an imaging finding;
  a minimum viewing time for each imaging finding;
  a minimum number of imaging planes an imaging finding has fixation locations in situations comprising wherein the imaging dataset comprises cross-sectional imaging planes;
  a determination of whether or not a structure had optimized display during a fixation location; and
  a determination of whether or not a predetermined sequence of fixation locations for each imaging feature has been achieved; and
instructions that alter the displayed image based on the relationship between the analyzed dataset and the predetermined criteria further comprising:
assigning a first visual representation adjustment logic to imaging finding(s) that have met the predetermined criteria, and
assigning a second visual representation adjustment logic to imaging finding(s) that have not met the predetermined criteria wherein the first visual representation adjustment logic is different from the second visual representation adjustment logic.

* * * * *